US011694339B2

(12) United States Patent
Schormans et al.

(10) Patent No.: US 11,694,339 B2
(45) Date of Patent: Jul. 4, 2023

(54) METHOD AND APPARATUS FOR DETERMINING BLOOD VELOCITY IN X-RAY ANGIOGRAPHY IMAGES

(71) Applicant: Pie Medical Imaging B.V., Maastricht (NL)

(72) Inventors: Ron Schormans, Heerlen (NL); Jean-Paul Aben, Limbricht (NL); Dennis Koehn, Voerendaal (NL)

(73) Assignee: Pie Medical Imaging B.V., Maastricht (NL)

( * ) Notice: Subject to any disclaimer, the term of this patent is extended or adjusted under 35 U.S.C. 154(b) by 384 days.

(21) Appl. No.: 15/971,275

(22) Filed: May 4, 2018

(65) Prior Publication Data
US 2018/0330507 A1  Nov. 15, 2018

(30) Foreign Application Priority Data

May 15, 2017 (EP) .................................... 17171126

(51) Int. Cl.
*G06T 7/579* (2017.01)
*A61B 6/00* (2006.01)
(Continued)

(52) U.S. Cl.
CPC ............... *G06T 7/20* (2013.01); *A61B 5/318* (2021.01); *A61B 6/481* (2013.01); *A61B 6/487* (2013.01);
(Continued)

(58) Field of Classification Search
CPC ..... A61B 5/0402; A61B 6/4441; A61B 6/481; A61B 6/487; A61B 6/504; A61B 6/507;
(Continued)

(56) References Cited

U.S. PATENT DOCUMENTS 5,150,292 A    9/1992  Hoffman
7,072,515 B2 *  7/2006  Al-Kofahi ............... G06K 9/48
                                                         382/128
(Continued)

FOREIGN PATENT DOCUMENTS

DE    102011083708 A1    4/2013

OTHER PUBLICATIONS

Hamarneh, G., Althoff, K., Gustavsson, T.: Snake Deformations Based on Optical Flow Forces for Contrast Agent Tracking in Echocardiography. In: Swedish Symposium on Image Analysis, pp. 45-48 (2000) (Year: 2000).*

(Continued)

*Primary Examiner* — Yi-Shan Yang
*Assistant Examiner* — Alexei Bykhovski
(74) *Attorney, Agent, or Firm* — Gordon & Jacobson, P.C.

(57) ABSTRACT

A method for quantitative flow analysis of a fluid flowing in a conduit from a sequence of consecutive image frames of such a conduit, where such image frames are timely separated by a certain time interval, the method comprising:
  a) selecting a start image frame and an end image frame from the sequence either automatically or upon user input;
  b) determining a centerline of the conduit in the start image frame;
  c) determining a centerline of the conduit in the end image frame;
  d) selecting a common start point on the centerline of the start image frame and on the centerline of the end image frame either automatically or upon user input;
  e) selecting an end point on the centerline of the start image frame;
  f) selecting an end point on the centerline of the end image frame;

(Continued)

g) calculating centerline distance between the start point and the end point of the start image frame;
h) calculating centerline distance between the start point and the end point of the end image frame; and
i) calculating a local flow velocity as a function of the centerline distances of g) and h) and a time interval between the start image frame and the end image frame.

A corresponding imaging device and computer program are also disclosed.

41 Claims, 14 Drawing Sheets

(51) Int. Cl.
   *G06T 7/20*      (2017.01)
   *G06T 7/00*      (2017.01)
   *A61B 5/318*     (2021.01)
(52) U.S. Cl.
   CPC .............. *A61B 6/504* (2013.01); *A61B 6/507* (2013.01); *A61B 6/5217* (2013.01); *A61B 6/541* (2013.01); *G06T 7/0016* (2013.01); *G06T 7/579* (2017.01); *A61B 6/4441* (2013.01); *G06T 2207/10016* (2013.01); *G06T 2207/10116* (2013.01); *G06T 2207/30104* (2013.01); *G06T 2207/30172* (2013.01)
(58) Field of Classification Search
   CPC .................. A61B 6/5217; A61B 6/541; G06T 2207/10016; G06T 2207/10116; G06T 2207/30104; G06T 2207/30172; G06T 7/0016; G06T 7/20; G06T 7/579
   See application file for complete search history.

(56) References Cited

U.S. PATENT DOCUMENTS

| | | | |
|---|---|---|---|
| 8,086,000 | B2 | 12/2011 | Weijers et al. |
| 8,787,641 | B2 | 7/2014 | Hof et al. |
| 2008/0319309 | A1 | 12/2008 | Bredno et al. |
| 2009/0221912 | A1* | 9/2009 | Nelson ................. A61B 5/7292 600/428 |
| 2014/0121513 | A1 | 5/2014 | Tolkowsky et al. |

OTHER PUBLICATIONS

"A Method towards Automated Thrombolysis in Myocardial Infarction (TIMI) Frame Counting Using 3D Reconstruction", Brinke et al, Computers in Cardiology 36, p. 653-656, 2009.
"A novel method for detecting R-peaks in electrocardiogram (ECG") signal", Manikandan et al, Biomedical Signal Processing and Control 7 (2012) 118-128.
"Automated Coronary Flow Assessment Using Planar X-Ray Angiography", Gerhard Albert Ten Brinke, PhD Thesis, University of Twente, Dec. 9, 2011, pp. 1-126.
"Automatic guide-wire detection for neurointerventions using low-rank sparse matrix decomposition and denoising", Zweng et al., Augmented Environments for Computer-Assisted Interventions pp. 114-123, Dec. 2015.
"Caas II: A Second Generation System for Off-line and On-line Quantitative Coronary Angiography", Gronenschild et al, Catheterization and Cardiovascular Diagnosis 33: 61-75 (1994).
"Detection of P and T-waves in Electrocardiogram", Mehta, et al., In: Proceedings of the World Congress on Engineering and Computer Science 2008.
"ECG gating at angiography for calculation of arterial lumen volume", Berglund et al, Acta Radiologica 198, 29:6.
"Effect of potential confounding factors on the thrombolysis in myocardial infarction (TIMI) trial frame count and its reproducibility", Abaci et al, Circulation 100 (22): 2219-2223.
"Image-based Co-registration of Angiography and Intravascular Ultrasound Images", Wang et al., In: IEEE Transactions on Medical Imaging, vol. 32, No. 12, Dec. 2013.
"Importance of the TIMI frame count: implications for future trials", Appleby et al, Curr Control Trials Cardiovasc Med. 2000; 1(1): 31-34.
"Intracoronary Doppler flow velocity measurements for the evaluation and treatment of coronary artery disease", Bach et al, Current Opinion in Cardiology 1995, 10: 434-442.
"Intraspecific scaling laws of vascular trees", Huo et al., J. R. Soc. Interface (2012) 9, 190-200.
"Linear algebra and its applications", Lay, 2012, 4th edition, p. 142-143, Addison-Wesley Longman.
"Lumen diameter of normal human coronary arteries: influence of age, sex, anatomic variation, and left ventricular hypertrophy or dilation", Dodge et al, Circulation 1992; 86: 232-246.
"Multiscale vessel enhancement filtering", Frangi, In Medical Image Computing and Computer-Assisted Intervention—MICCAI 1998, Lecture Notes in Computer Science, vol. 1496 pp. 130-137.
"Non-rigid image registration", Fischer, et al., In: http://www.mic.uni-luebeck.de/uploads/ tx_wapublications/ 2006-KOREA-BF.pdf, 2006.
"Quantification of arterial flow using digital subtraction angiography", Bonnefuis et al., Medical Physiology 39 (10), Oct. 2012.
"Robust and fast contrast inflow detection for 2D x-ray fluoroscopy", Chen et al, MICCAI 2011, Part 1, pp. 243-250.
"The Thrombolysis in Myocardial Infarction (TIMI) trial. Phase I findings. TIMI Study Group", The New England Journal of Medicine, Apr. 4, 1985, 312(14):932-6.
"TIMI Frame Count: A Quantitative Method of Assessing Coronary Flow", Gibson et al., Circulation, vol. 93, Issue 5, 879-888 (1996).
"X-ray videodensitometric methods for blood flow and velocity measurement: A critical review of literature", Shpilfoygel et al., Medical Physics vol. 27, No. 9, Sep. 2000.
European Search Report of application No. EP1717126 dated Apr. 10, 2018.

* cited by examiner

| $V_{local}$ $I_2$ $I_1$ | 13 | 14 | 15 | 16 | 17 | 18 | 19 | 20 |
|---|---|---|---|---|---|---|---|---|
| 12 | 147 | 178 | 172 | 195 | 198 | 223 | 185 | 180 |
| 13 | x | 209 | 184 | 211 | 211 | 238 | 191 | 185 |
| 14 | x | x | 159 | 212 | 211 | 245 | 188 | 181 |
| 15 | x | x | x | 265 | 238 | 274 | 195 | 185 |
| 16 | x | x | x | x | 211 | 279 | 172 | 165 |
| 17 | x | x | x | x | x | 347 | 153 | 150 |
| 18 | x | x | x | x | x | x | 0 | 51 |
| 19 | x | x | x | x | x | x | x | 144 |

Fig. 7

METHOD AND APPARATUS FOR DETERMINING BLOOD VELOCITY IN X-RAY ANGIOGRAPHY IMAGES

CROSS-REFERENCE TO RELATED APPLICATIONS

The present application claims priority from EP Patent Application No. 17171126.0, filed on May 15, 2017, herein incorporated by reference in its entirety.

BACKGROUND

1. Field

The present application relates to the technical field of medical imaging, particularly angiography imaging, although it can find application in any field where there is the need to quantify flow in a conduit such as in non-destructive testing applications.

2. State of the Art

Coronary artery disease (CAD) is one of the leading causes of death worldwide. CAD generally refers to conditions that involve narrowed or blocked blood vessels that can lead to reduced or absent blood supply to the sections distal to the stenosis resulting in reduced oxygen supply to the myocardium, resulting in, for instance, ischemia and myocardial infarction. Myocardial infarction (MI), commonly known as a heart attack, occurs when the blood flow stops to a part of the heart causing irreversible damage to the heart muscle. Approximately 1.5 million cases of MI occur annually in the United States alone.

Presently, X-ray angiography is the imaging modality used during treatment of stenotic (narrowed) coronary arteries by means of a minimally invasive procedure also known as percutaneous coronary intervention (PCI). During PCI, an interventional cardiologist feeds a deflated balloon or other device on a catheter from the inguinal femoral artery or radial artery up through blood vessels until they reach the site of blockage in the artery. X-ray imaging is used to guide the catheter threading. PCI usually involves inflating a balloon to open the artery with the aim to restore unimpeded blood flow. Stents or scaffolds may be placed at the site of the blockage to hold the artery open.

To have a complete understanding of CAD, a clinician must be able to evaluate coronary anatomy, ventricular function and coronary blood flow. X-ray angiography remains the standard imaging technique for obtaining information on the first two factors. Although visual assessment of percentage diameter percentage diameter coronary stenosis suffers from significant intraobserver and interobserver variability, quantitative coronary analysis (QCA) provides accurate and objective measurement of arterial geometry. The third factor, coronary blood flow, is rarely measured directly.

A method for assessment of coronary blood flow in the catheterization laboratory is by means of intracoronary Doppler measurements techniques. These techniques involve percutaneously inserting a Doppler-transducing wire inside the coronary artery and measuring the blood velocity inside the coronary artery as described by Bach et al, "Intracoronary Doppler flow velocity measurements for the evaluation and treatment of coronary artery disease", Current Opinion in Cardiology 1995, 10: 434-442. Intracoronary Doppler measurements, however, has some disadvantages. The technique is associated with the additional cost of a Doppler wire which can only be used once. Furthermore, Doppler-based assessment of coronary flow velocity requires additional invasive catheterization with the associated cost and procedure time. Moreover, Doppler-based assessment of coronary flow velocity relies on average peak velocity and does not take into account changes in velocity profile or vessel area which are usually occurring in patients with CAD.

Coronary blood flow estimation based on X-ray angiographic image data would be preferable, since this would require no additional invasive catheterization with the associated cost and procedure time. For many years, coronary blood flow has been simply assessed by the thrombolysis in myocardial infarction (TIMI) flow grade. This simple qualitative grading of angiographic coronary flow rates to assess the efficiency of reperfusion therapy, such as PCI, has been widely used to gauge the restoration of perfusion in clinical trials "The Thrombolysis in Myocardial Infarction (TIMI) trial. Phase I findings. TIMI Study Group", The New England Journal of Medicine, 1985 Apr. 4, 312(14):932-6. This method assessed the amount of frames required for the contrast to reach a standardized distal coronary landmark in the diseased vessel. This assessment is performed by visually assessing the number of frames within a two-dimensional x-ray angiographic image run, which are required for the contrast to reach a standardized distal coronary landmark of the diseased vessel. The number of frames is based upon an x-ray cine filming rate of 30 frames per second. Thus, a frame count of 30 would mean that one second was required for dye to traverse the artery. The TIMI flow grade categorized the patient's coronary flow into one of four different categories namely grade 0 (no flow), grade 1 (penetration without perfusion), grade 2 (partial perfusion) or grade 3 (complete perfusion).

However, this method is very subjective due to the high observer variability in the determination of the first and last frame used for the TIMI counting. Furthermore, this method is categorical, and no continuous angiographic index of coronary flow is given.

To overcome these limitations, Gibson et al, "TIMI Frame Count: A Quantitative Method of Assessing Coronary Flow", Circulation, Volume 93, Issue 5, 879-888 (1996) developed a more objective and continuous variable of coronary blood flow called the corrected TIMI frame count (CTFC).

In this method the TIMI frame count is adjusted for the vessel length. A correction factor is applied to compensate for the longer length of the left anterior descending artery (LAD) compared with the circumflex and the right coronary arteries as described in Appleby et al, "Importance of the TIMI frame count: implications for future trials", Curr Control Trials Cardiovasc Med. 2000; 1(1): 31-34.

However, this corrected version is still based on the visual assessment of the frames by the clinician. Furthermore, several variables such as injection force, sex, hemodynamics, body size and contrast agent type may impact the CTFC as for instance described in Abaci et al, "Effect of potential confounding factors on the thrombolysis in myocardial infarction (TIMI) trial frame count and its reproducibility", Circulation 100 (22): 2219-2223.

To develop a more robust quantification of coronary blood flow, various research in the field of coronary velocity determination for angiography has taken place over the years. A good overview of most early work in this field can be found in Shpilfoygel et al., "X-ray videodensitometric methods for blood flow and velocity measurement: A critical review of literature", Medical Physics vol 27, No. 9, September 2000. This article gives an overview of several different approaches in the determination of coronary velocity and flow. Shpilfoygel et al. distinguish two major classes of blood flow velocity algorithms; tracking algorithms and computational algorithms. The latter class, the computational algorithms, make use of models, mass and volume equations. These approaches rely on assumptions of for instance mass and volume, and/or require additional information, which make these methods not suitable for fast assessment of coronary blood flow in a clinical setting such as during a coronary intervention in a catheterization laboratory.

Several tracking algorithms are available, which focus on the displacement of the contrast bolus in the vessel. The bolus transport time algorithms determine the velocity by measuring the time that it takes for the bolus to travel from one fixed location to a second fixed location within the vessel. This method is not robust for pulsatile flows and requires densitometric information for all frames at two locations to acquire two bolus density curves. To achieve these bolus intensity curves, accurate tracking of the measurement locations in all frames is required and this computational expensive and time consuming. The continuous velocity determination from two-dimensional time-distance parametric images algorithms are too complex to apply in a clinical case. The droplet technique is not applicable into a clinical setting because of the injection method that is required by this method does not match clinical practice. From Shpilfoygel et al., the drawbacks of several techniques can be learned, such as that most methods focus on bolus displacement between subsequent frames, this is not suitable for pulsatile flows. Another approach focuses on the contrast concentration during a whole cardiac cycle and an empirical determined densitometric level is used to determine the traveled bolus distance. The latter method is sensitive for local densitometric deviations.

A similar approach based on bolus arrival time is used more recently by Ten Brinke et al, "A Method towards Automated Thrombolysis in Myocardial Infarction (TIMI) Frame Counting Using 3D Reconstruction", Computers in Cardiology 36, p. 653-656, 2009. In this article, Brinke et al. determines the TIMI frame count (a measure of velocity) by drawing and following a centerline through multiple image frames through time, and deriving the mentioned frame count by following decreases in contrast intensity over time. In addition to this, Brinke et al. uses a 3D reconstruction of the coronary vessel to improve distance measured along the coronary vessel. This method is usually called a bolus arrival time-based method, as it keeps track of a couple of fixed spatial points over time and marks the moments in time when changes in the points occur.

A similar method is used by Fieselmann et al. in German Patent Application DE102011083708. This document discloses a method for the assessment of contrast diffusion in angiography images to determine and visualize blood flow parameters such as for instance blood flow, blood flow velocity and contrast agent dispersion. This method also relies on two spatially fixed points, and measures the passage of contrast agent in those two points. In this case, the measurements combined with distance are not only used to get velocity rates, but also to get a contrast agent dispersion variable, which is used for calculating the volume in which the contrast has spread, being an indirect indication of flow and velocity.

However, the approaches described above to assess coronary blood flow by means of X-ray Angiography, suffer from several limitations.

First, most methods focus on two or more spatially fixed points and track the intensity changes of those points through time. Making these approaches very vulnerable to the temporal resolution (cine framerate) of the x-ray angiographic acquisition system. Since the introduction of TIMI, the cine framerate gradually decreased to 7.5-15 frames per second, due to technical improvements with the aim to reduce X-ray exposure to the patient. This reduction in cine framerate introduced two drawbacks in the assessment of coronary flow by TIMI frame count and method similar. With respect to TIMI frame count, the standardized method to assess blood flow only applies with a cine framerate of 30 frames per second. More importantly, reduction in cine framerate directly negatively effects the temporal resolution of x-ray angiography. For instance, a cine framerate of 7.5 frames per second results in a temporal resolution of 133 milliseconds as compared to 33 milliseconds as obtained with 30 frames per second. In normal use of a cine framerate of 15 frames per second, large offsets in measured coronary flow velocity can arise depending on the time interval chosen and the exact moment of acquisition.

Secondly, for automatic approaches such as Brinke et al. and by Fieselmann et al., robust image registration is needed, as coronary vessels are constantly in motion due to for instance the cardiac cycle, breathing cycle, and patient movements.

To summarize, all the above methods have a dependency on temporal resolution for their accuracy, require image registration or are limited in timing scope by the positions of the reference points chosen. Furthermore, some methods require biplane image acquisition.

There is therefore a need for a more accurate, fully objective and reproducible approach to determine blood velocity in X-ray angiographic images.

SUMMARY

It is thus an object of embodiments herein to accurately determine the flow velocity in a conduit from a sequence of two-dimensional or three-dimensional images, particularly blood velocity in a vessel from two-dimensional angiographic images, which is independent on temporal resolution and biplane image acquisition and can cope with conduit movement.

In accordance with embodiments herein, devices, computer program products and computer implemented methods are provided for quantitative flow analysis of a fluid flowing in a conduit from a sequence of consecutive image frames of such a conduit, which such image frames are timely separated by a certain time interval, the devices, program products and methods comprising, under control of one or more computer systems configured with specific executable instructions, which involve selecting a start image frame and an end image frame from the sequence either automatically or upon user input;

determining a centerline of the conduit in the start image frame;

determining a centerline of the conduit in the end image frame;

selecting a common start point on the centerline of the start image frame and on the centerline of the end image frame either automatically or upon user input;

selecting an end point on the centerline of the start image frame;

selecting an end point on the centerline of the end image frame;

calculating centerline distance between start point and end point of the start image frame;

calculating centerline distance between start point and end point of the end frame; and calculating a local flow velocity as a function of the centerline distances and time interval between the start image frame and the end image frame.

In an embodiment, the sequence of image frames contains information for determining the distribution over time of a contrast agent travelling in the conduit, the start image frame and the end image frame relate to different distributions of contrast agent in the conduit from a proximal point to a distal point located on the centerline of the start image frame and of the end image frame. The end point in the start image frame and the end point in the end image frame can be, for example, identified by the front of the contrast agent distal to the common start point.

In an embodiment, intensity versus centerline distance graphs from the start point are calculated in both the start image frame and the end image frame. The end point in either the start image frame or the end image frame can thus be selected by setting a threshold and identifying the centerline distance corresponding to the point having intensity equal to such a threshold.

The common start point in the start image frame and the end image frame may be selected by performing one or more operations selected from the group consisting of: automatically detecting tip of a contrast injection catheter, automatically detecting an anatomical point such as point of a vessel bifurcation, and elaborating a user input.

The sequence of image frames preferably contains digitally subtracted image frames or the method further comprise the step of digitally subtracting the image frames of the sequence from a mask frame or multiple mask frames to obtain digitally subtracted image frames to enhance the flow in the conduit and thus increase the resolution.

According to an embodiment, one or more additional local flow velocities can be calculated based on different image frame selection to provide a map of flow velocities as a function of time.

Alternatively or in combination, the flow velocity can be adjusted by a correlation factor to determine an average velocity over a period of time. When the conduit is a blood vessel, the sequence preferably comprises bi-dimensional or three-dimensional image frames covering one or more heart cycles and the average velocity is calculated over a period of time corresponding to the one or more heart cycles.

The correlation factor can be calculated, for example, by processing an input database of known velocity profiles.

Advantageously, the local flow velocity or the average velocity can be propagated to other segments of the conduit to estimate flow velocity in such segments, for example for those parts that are hidden or masked and thus cannot be properly seen in the image frames.

More in general the local flow velocities may be used for further quantitative processing, for example for volumetric flow analysis, CFR, CFD or the like calculations.

Embodiments also relate to a computer product directly loadable into the memory of a digital computer and comprising software code portions for performing the method according to embodiments herein when the product is run on a computer.

According to an aspect, embodiments relate to an imaging device, typically a X-ray or MM device, more typically an X-ray device for angiography, for acquiring contrast enhanced two dimensional or three dimensional sequences of image frames, the device comprising an acquisition module for obtaining a plurality of image frames of a vessel perfused by a contrast agent, a timing module for driving the acquisition module to obtain image frames temporally shifted of a known time interval after a trigger event, input for receiving from the user indication for the selection of a start image frame and an end image frame of the sequence and/or a selection module for automatically selecting a start image frame and an end image frame of the sequence, the device further comprising a processor programmed to:

determine a centerline of the vessel in the start image frame;

determine a centerline of the vessel in the end image frame;

select a common start point on the centerline of the start image frame and on the centerline of the end image frame either automatically or upon user input;

select an end point on the centerline of the start image frame; select an end point on the centerline of the end image frame;

calculate centerline distance between the start point and the end point of the start image frame;

calculate centerline distance between the start point and the end point of the end image frame; and calculate a local flow velocity as a function of centerline distances and time interval between the start image frame and the end image frame.

Embodiments herein provide that the common start point in the start image frame and the end image frame is selected by performing one or more operations selected from the group consisting of: automatically detecting tip of a contrast injection catheter, automatically detecting an anatomical point such as point of a vessel bifurcation, elaborating a user input.

The end points in start image frame and the end image frame may be selected by elaborating a user input and/or automatically detecting drop points in graphs representing intensity versus centerline distance from the start point in both the start image frame and the end image frame.

The imaging device may advantageously comprise a digital subtraction angiography module configured to compute a mask frame and subtract such a mask frame or multiple mask frames from the image frames to obtain a sequence of flow-enhanced frames.

According to embodiments herein, the device further comprises an ECG module to synchronize acquisition with heart cycle, the processor being configured to calculate local velocities for a plurality of couples of image frames of the sequence related to one or more heart cycles.

According to embodiments herein, the device further comprises a module to synchronize contrast injection with the heart cycle, ensuring contrast injection will always start at the same moment within the cardiac cycle.

The inventors have recognized that an image sequence acquired by an X-ray system contains two different temporal resolutions. First, the amount of frames acquired during one second is defined as the cine frame rate resulting in a temporal cine frame rate resolution ($t_{cineframe}$). Second, the duration required to acquire a single frame within a cine image run ($t_{acquisition}$). In current state of the art X-ray angiographic system, the $t_{acquisition}$ is in the order of a few milliseconds. Furthermore, the inventors have recognized that the $t_{acquisition}$ is independent from $t_{cineframe}$. Therefore, in one of the embodiments, this difference in temporal resolutions is exploited by assessment of the coronary artery contrast bolus front within an x-ray angiographic frame (having a temporal resolution of $t_{acquisition}$), and being less dependent on $t_{cineframe}$. The contrast bolus front is the furthest distal (downstream the vessel tree) position in the vessel of interest in a given angiographic frame in which the contrast is still visible. Furthermore, some embodiments are able to determine blood velocity on an acquisition frame to frame basis, and take into account effects caused by the heart contraction cycle.

BRIEF DESCRIPTION OF THE DRAWINGS

The characteristics of the embodiments herein and the advantages derived therefrom will be more apparent from the following description of non-limiting embodiments, illustrated in the annexed drawings.

FIG. 7 shows a matrix containing selected $v_{local}$ values for various combinations of input image frames.

DETAILED DESCRIPTION OF THE PREFERRED EMBODIMENTS

Figure 1:
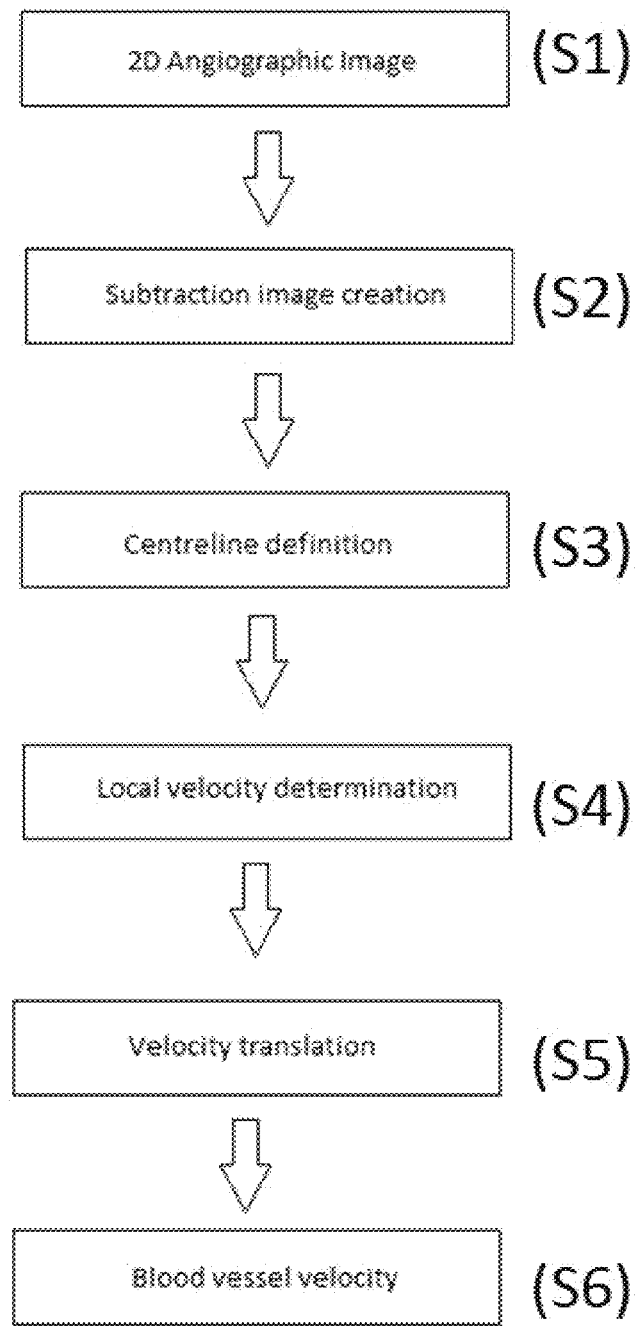
FIG. 1 shows a flow chart of a method for determining flow velocity in accordance with an embodiment herein.
Figure 3:
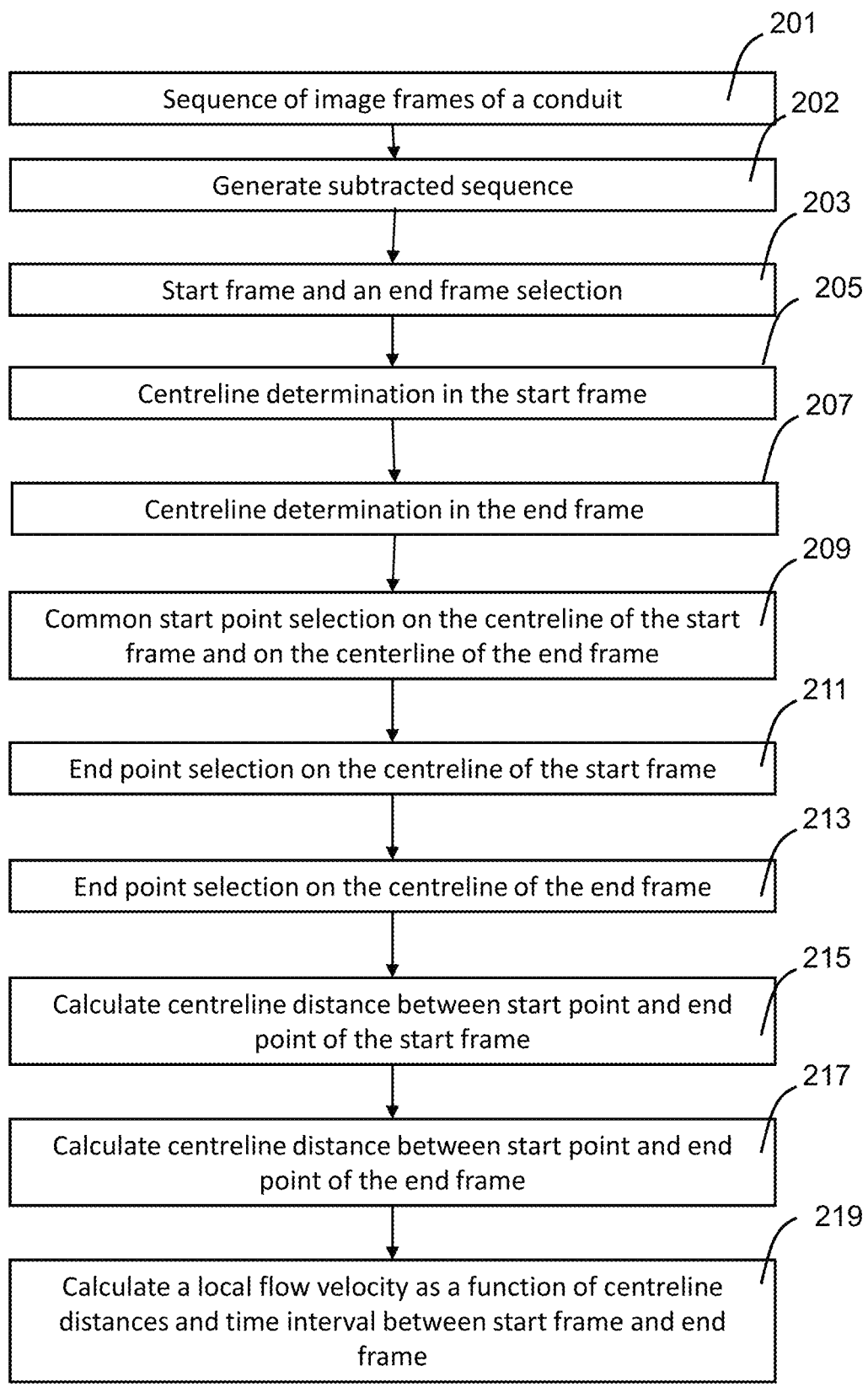
FIG. 3 shows a flow chart of a method for determining flow velocity in accordance with another embodiment herein.

FIGS. 1 and 3 show flow charts illustrating the operations according to embodiments of the present application. The operations employ an imaging system capable of acquiring and processing two-dimensional images of a vessel organ (or portion thereof) or other object of interest. For example, a single plane angiographic system can be used as those manufactured, for example, by Philips (Allura Xper FD).

Figure 2:
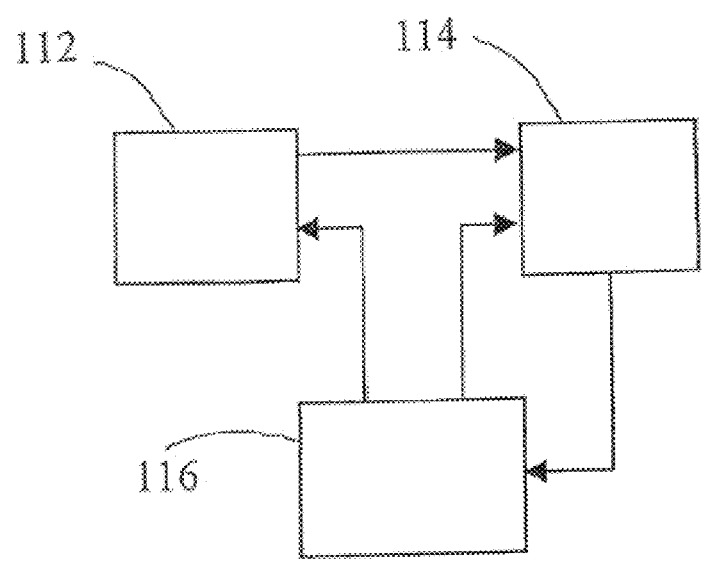
FIG. 2 is a block diagram of an example x-ray cinefluorographic unit accordance with an embodiment herein.

FIG. 2 is a functional block diagram of an exemplary single plane angiographic system, which includes an angiographic imaging apparatus 112 that operates under commands from user interface module 116 and will provide data to data processing module 114. The single plane angiographic imaging apparatus 112 captures a two-dimensional X-ray image run of the vessel organ of interest for example in the postero-anterior (PA) direction. The single plane angiographic imaging apparatus 112 typically includes an X-ray source and detector pair mounted on an arm of a supporting gantry. The gantry provides for positioning the arm of the X-ray source and detector at various angles with respect to a patient who is supported on a table between the X-ray source and detector. The data processing module 114 may be realized by a personal computer, workstation or other computer processing system. The data processing module 114 includes one or more processors and memory that stores program instructions to direct the one or more processors to perform the operations described herein. The data processing module 114 also includes a display to present information to a user, such as the images, indicia, data and other information described herein and illustrated in the figures. The data processing module 114 also includes a user interface to receive inputs from the user in connection with operations herein, such as controlling operation of the imaging apparatus 112, selecting projection perspectives to be used when obtaining complementary images and the like. The data processing module 114 may correspond to or include portions of one or more of the systems described within the patents and publications referenced herein and incorporated by reference. The data processing module 114 processes the two-dimensional image captured by the single plane angiographic imaging apparatus 112 to generate data as described herein. The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of FIG. 1 or 3 as described below. The operations of FIG. 1 or 3 can also be carried out by software code that is embodied in a computer product (for example, an optical disc or other form of persistent memory for instance an USB drive or a network server). The software code can be directly loadable into the memory of a data processing system for carrying out the operations of FIG. 1 or 3.

The embodiments are now disclosed in detail by way of a non-limiting example. In this example, it is assumed to have at disposal a two-dimensional angiographic image run of an object of interest (S1, 201). For example, the two-dimensional angiographic image data may be obtained in real time from an angiographic imaging system. Optionally, pre-recorded two-dimensional angiographic image data may be obtained from a local memory, a database, a network server or otherwise. This two-dimensional angiographic image run contains multiple frames covering multiple heart phases. Any image device capable of providing two-dimensional angiographic image runs can be used for this purpose. For example, a single plane angiographic system can be used such as those manufactured, for example, by Philips (Allura Xper FD).

Figure 4:
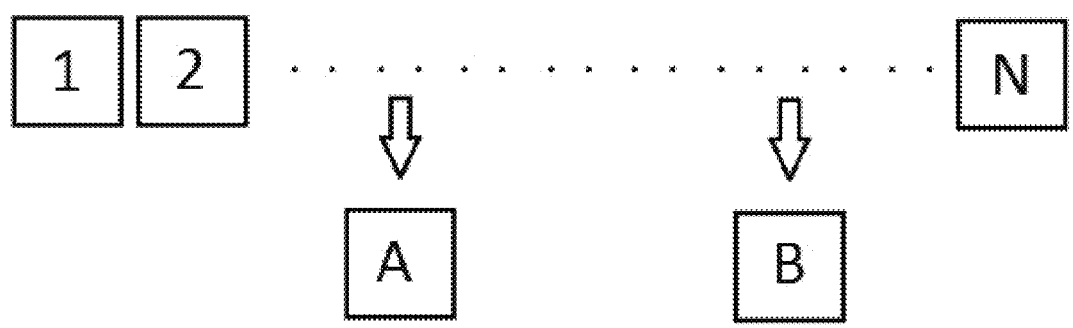
FIG. 4 shows the selection of the start and end frame from a two-dimensional angiographic image run.

From the acquired two-dimensional angiographic image run (S1), subtraction frames are preferably calculated to enhance the flow (S2) and a start frame A and end frame B are selected (203) as it can be seen in FIG. 4. Then a centerline along a vessel of interest is indicated in the selected two frames (205, 207) of the image run (S3). From this input, blood velocity can be determined in the vessel of interest. The velocity is determined by looking at a combination of distance covered over time between frames (S4, 219). An optional translation based on the time between frame A and frame B in relation to the cardiac heart cycle can be performed as shown in operation S5. The information on the cardiac heart cycle can be determined, for example, from an Electrocardiography (ECG) signal linked to the two-dimensional angiographic image run. This results in a patient specific, heart phase independent, blood vessel velocity value (S6). These separate steps, and some variations on these basic steps of the embodiment, are described below.

The embodiment uses X-ray angiographic image analysis to determine average blood velocity in a targeted blood vessel or vessel of interest. Therefore, subtraction angiographic frames and ECG signal corresponding with the X-ray angiographic image run are preferred for the optimal performance of the blood velocity determination method as shown in S2 and 202. This step contributes to enhance image flow quality, but can be obviously omitted. Other imaging modalities can be used, for example MRI or computed tomography or x-ray rotational angiography, to obtain similar results.

In traditional X-ray angiography, images are acquired by exposing an area of interest with time-controlled X-rays while injecting contrast medium into the blood vessels. The image obtained would also include all overlying structure besides the blood vessels in this area. This is useful for determining anatomical position and variations, but unhelpful for visualizing blood vessels accurately. Digital subtraction angiography (DSA) uses a computer technique which compares an X-ray image of a region of the body before and after radiopaque iodine-based dye has been injected intravenously into the body. Tissues and blood vessels on the first image are digitally subtracted from the second image (mask frame, the image which contains no radiopaque iodine), leaving a clear picture of the artery which can then be studied independently and in isolation from the rest of the body.

DSA can for instance be calculated from the two-dimensional angiographic image run and most X-ray angiographic systems include an imaging protocol to directly generate DSA. However, DSA uses a static mask frame and is therefore not able to compensate for cardiac motion which occurs during the acquisition.

Another method for the creation of a subtraction image run is for instance based on Digital Imaging and Communications in Medicine (DICOM) information that is available for the image run. DICOM is a standard for handling, storing, printing and transmitting information in medical imaging. It includes a file format definition and a network communications protocol. For instance, ECG data (e.g., represented as a list of points) can be stored in the DICOM.

Figure 5:
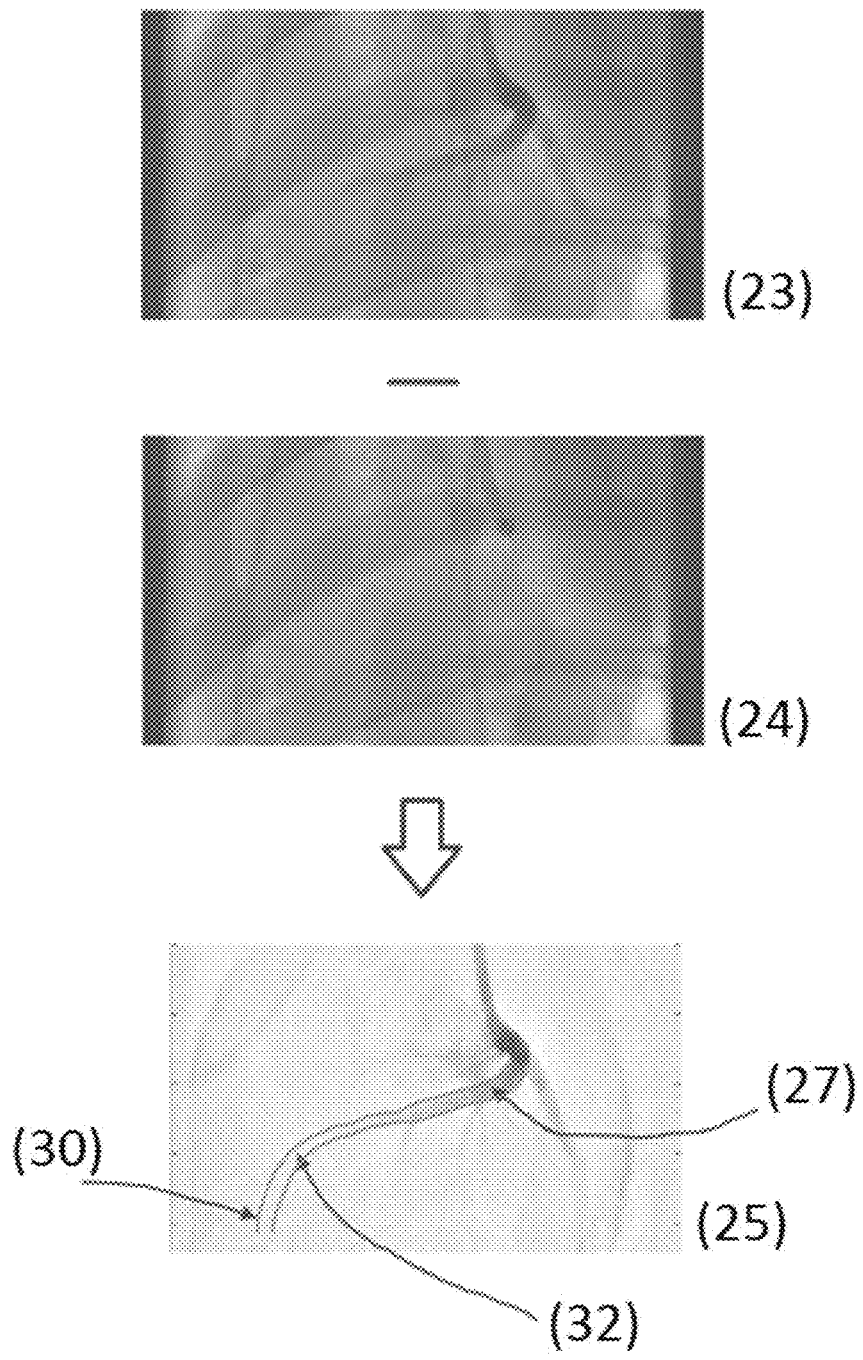
FIG. 5 shows an example of a mask frame that is subtracted from an angiographic frame to result in a subtracted frame.

If the angiographic image run has ECG information available in the DICOM, and the contrast injection starts after a full heart cycle within the X-ray angiographic image run, multiple mask frames can be created using this heart cycle before contrast injection. This moment of contrast injection is henceforth referred to as $T_c$. When not indicated by the user, alternatively, this $T_c$ can be detected automatically by methods described in literature, for example by Chen et al, "Robust and fast contrast inflow detection for 2D x-ray fluoroscopy". MICCAI 2011, Part 1, pp 243-250. In this article, a vesselness filter working on first order derivative responses which occur when a vessel is filled with contrast agent, detects the number of vessels. By monitoring the response of such a vesselness filter, which shows a large increase at the moment of contrast injection, as vessels suddenly become visible, the moment of contrast injection can be pinpointed. By matching frames after contrast injection to a moment in the ECG heart cycle, one or more specific mask frames (FIG. 5, reference 24) can be subtracted from one or more angiographic frames (FIG. 5, reference 23) after contrast injection. This removes any movement in the patient caused by for instance cardiac motion, and creates one or more improved subtraction frames (FIG. 5, reference 25). Alternatively, if no complete heart cycle or if no ECG graph is available before the moment of contrast injection $T_c$ as determined above, a single mask frame is computed by determining a maximum intensity frame from all time frames before the moment of measurement (subtraction start frame). Such maximal intensity frame mask is created by looking at every pixel through the number of input frames, and assigning the maximum pixel value to the pixel at the same position in the mask frame. Any contrast already injected also causes a drop in image intensity, and will not show up in this maximal intensity mask. In the subtracted image run, or in the original sequence, two frames can be selected as shown in FIG. 4. One frame, representing the image within the image run showing the contrast bolus front proximal the vessel of interest (A), and one frame further down the target vessel representing the image within the image run showing the contrast bolus front distal to the vessel of interest (B).

Figure 11:
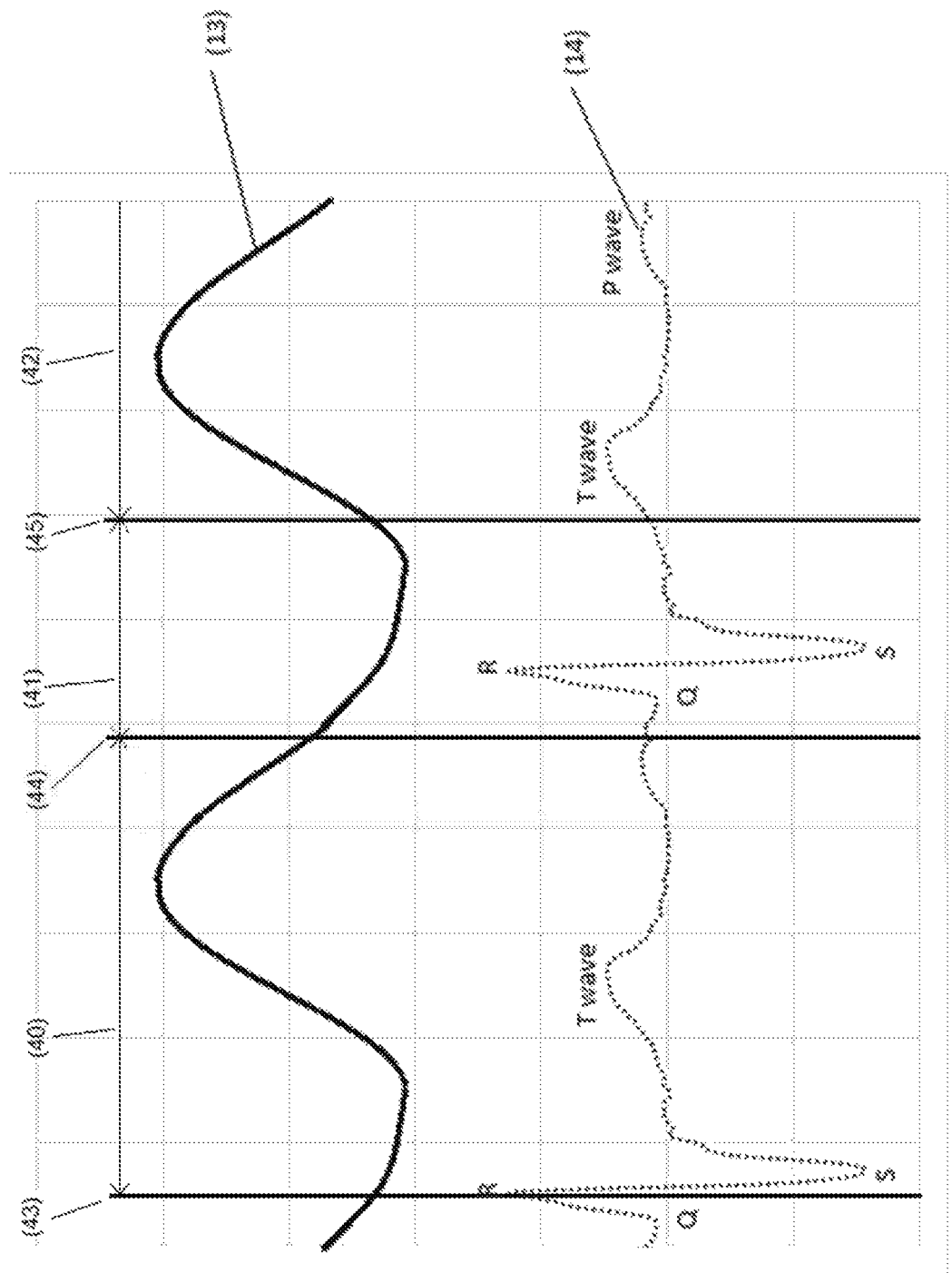
FIG. 11 shows an example of a generic blood velocity profile linked to a heart phase in the form of an ECG diagram including the P- and T-wave.

Optionally, the start frame A can be selected automatically being the frame in which the contrast injections starts ($T_c$). If the angiographic image was created while using ECG gated contrast injection, the process of identifying the start frame A can become easier and automated. An example of an ECG gated contrast injector is for instance a Medrad Mark IV injector (Bayer) as described by Berglund et al in "*ECG gating at angiography for calculation of arterial lumen volume*", Acta Radiologica 198, 29:6. Such an ECG gated injector receives the ECG signal from the patient and the injection of contrast liquid is triggered for instance by the R-wave in the QRS complex. Control of exact timing can be performed by setting a delay (FIG. 11, reference 40) between the detection of R-wave (FIG. 11, reference 43) and the start of the contrast injection (FIG. 11, reference 41) The contrast is then injected within a short time window within one cardiac cycle (e.g. ⅕ the time of one cardiac cycle, FIG. 11, reference 41). In this example, the frame $T_c$ is illustrated in FIG. 11, reference 44. The advantage of an ECG gated contrast injection is to assure that the contrast enters the blood vessel in an exact moment within the cardiac cycle. The ideal moment for this contrast injection is around the time the QRS complex triggers heart contraction, the systolic coronary blood flow phase (FIG. 11, reference 41). At this time, blood flow in the coronaries is close to its minimum, as shown in FIG. 11, reference 13. This figure describes a generic average velocity curve, though it is possible to use specific delays (40) between the detection of R-wave (43) and the start of the contrast injection. For the different coronary arteries (e.g. left coronary artery, right coronary artery, coronary circumflex, etc.) the moment of minimal coronary velocity can occur at a different moment within the cardiac cycle. By using specific delays (40) it is possible to enable optimal contrast injection specific for the coronary artery of interest Alternatively, the start frame A is selected at the image frame in which the ECG gated contrast injection finalized (FIG. 11, reference 45). Utilizing this approach further eliminates the impact of contrast injection velocity of the blood velocity calculated (FIG. 11). Selecting the start frame A after the contrast injection has finished, makes sure the velocity measured (FIG. 11, reference 42) is actual blood flow velocity, and not part of the contrast injection velocity. If not accounted for, the velocity due to the contrast injection can impact the measured coronary blood velocity, as noted in Bonnefuis et al, "Quantification of arterial flow using digital subtraction angiography", Medical Physiology 39 (10), October 2012. This also maximizes the distance over which contrast propagation can be measured, starting directly at the injection point of the contrast fluid.

The end frame B can be selected manually, or set at a fixed time subsequent to frame A, for example an entire heart cycle, based on heart rate or the ECG signal of the patient.

In both these frames A and B, a centerline is created along the contrast agent including the contrast bolus front (FIG. 6, reference 2), starting from a start point in both frames (FIG. 6, reference 1) as shown in operation S3 of FIG. 1 or 205, 207 of FIG. 3. This starting points in frame A and B should represent an identical anatomical position (FIG. 3, reference 209), which can be achieved using several methods known in the art.

For instance, by automatically detecting the tip of the contrast injection catheter as anatomical position in both images as taught in Zweng et al., "Automatic guide-wire detection for neurointerventions using low-rank sparse matrix decomposition and denoising", Augmented Environments for Computer-Assisted Interventions pp 114-123, December 2015 or Wang et al., "Image-based Co-registration of Angiography and Intravascular Ultrasound Images", In: IEEE Transactions on Medical Imaging, vol. 32, no 12, December 2013, which uses subtraction images with noise filtering and a robust principal component analysis to determine regions of interest in which the guide wire might be present, resulting in a binary image of the guide wire. This method makes selecting an anatomically identical point at the start of the vessel tree very reliable. The complete subject matter of the publication referenced herein is incorporated by reference herein in its entirety.

Alternatively, if a starting point further down the vessel tree is desired than the catheter tip, an automatically detected point of a bifurcation is a second method to get an anatomically matching starting point. This point of bifurcation detection can for instance be detected as described in U.S. Pat. No. 8,086,000. In this patent a bifurcation is detected by deriving the contours and centerline of the vessel and determining the start and end of bifurcation. Then the angles between the various branches of the bifurcation are determined and the position of the center of bifurcation is determined. The complete subject matter of the patent referenced herein is incorporated by reference herein in its entirety.

As another alternative method, the starting points can be indicated manually by the user.

Figure 6:
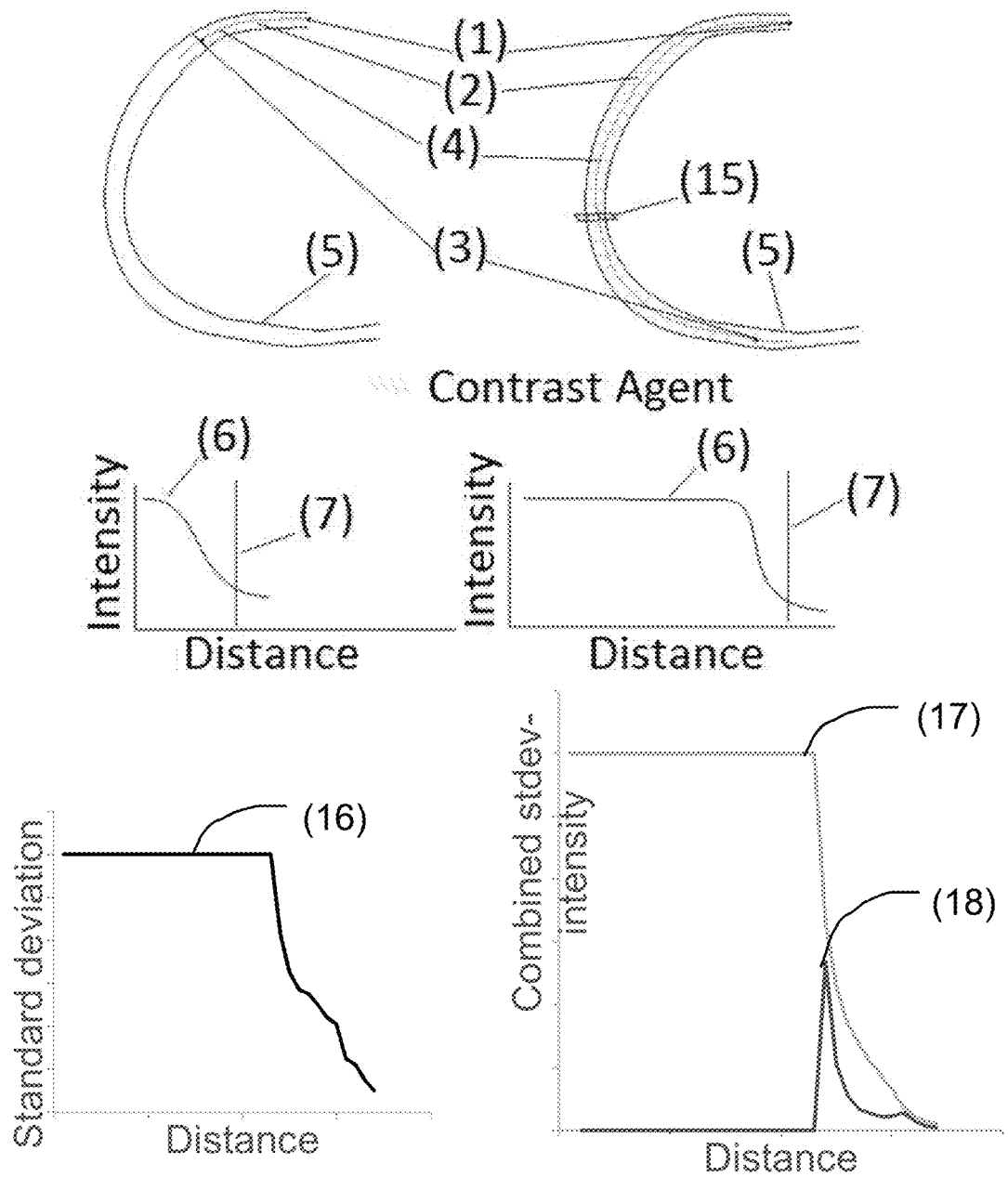
FIG. 6 shows the centerline creation along the contrast agent.

The created centerline (FIG. 6, reference 4) must continue until and through the visible contrast agent front (FIG. 6, reference 3), travelling through the target vessel. The intensity profile along this centerline can be plotted into distance/intensity graphs, resulting in graphs as can be seen in FIG. 6, reference 6. The intensity values of these graphs are calculated by averaging the intensities within a small region of interest around every point on the centerline (FIG. 6, reference 15).

An end point (representing the contrast bolus front within the conduit) based on contrast intensity can, for instance, be manually indicated by the user (FIG. 3, reference 211, 213). The user can for instance indicate an end point in the angiographic frame or in the distance/intensity graphs (FIG. 6, reference 6).

Alternatively, an end point can be automatically defined. Along the vessel centerline, small regions of interest extending slightly beyond the vessel borders are defined, as earlier described in S3, 211, 213 and FIG. 6, reference 15. By extending these regions a little further away from the centerline through the vessel borders (FIG. 6, reference 15), it is possible to include both a part of the vessel and a part of the background in such region. As such, these regions of interest will cover two regions; the region within the vessel (dark) as well as the region outside of the vessel (background, light). As long as the vessel is filled with contrast, the inside of the vessel will remain dark (FIG. 5, reference 27). The part of the vessel in which the contrast bolus front still needs to travel (FIG. 5, reference 30), will be the same intensity as the background (light) (FIG. 5, reference 32). This is best captured by computing the standard deviation-distance graph (FIG. 6 reference 16). In this graph the standard deviation within each region of interest around every point on the centerline (FIG. 6, reference 15) is calculated, which will drop once the contrast bolus front is reached. This drop point (end point) can be automatically detected, marking the contrast bolus front with greater reproducibility than by visual determination. The end point locks a distance which the contrast agent travelled with a temporal resolution of $t_{acquisition}$ of the given frame. As $t_{acquisition}$ for typical X-ray imaging systems is in the range of milliseconds, this creates a very accurate moment of imaging in time and a very accurate distance measurement of the contrast agent. The automatic detection of the above-mentioned drop point can be based on a predefined threshold value within the standard deviation-distance graph. Alternatively, a combined standard deviation-intensity distance graph can be computed (FIG. 6, reference 17), for instance by multiplying the distance graph with the standard deviation graph. This graph will emphasize the drop location. The drop point can be defined as the location of the maximum absolute derivative of the combined standard deviation-intensity distance graph (FIG. 6, reference 18).

Given the contrast agent presence in both frames, this is combined with the time interval between the frames to generate a velocity in the blood vessel between the two marked end points as described in operation S4 or 219:

$$v_{local} = \frac{s_2 - s_1}{t_2 - t_1} \quad \text{(eq. 1)}$$

where $v_{local}$ is the velocity measured over the vessel segment between the contrast fronts in the given input frames,
$s_1$ the distance measured in the first frame (frame A),
$s_2$ the distance measured in the second frame (frame B),
$t_1$ the timestamp of the start of acquisition of the first frame, and
$t_2$ the timestamp of the start of acquisition of the second frame.

The timestamps $t_1$ and $t_2$ can, for instance, be extracted from appropriate fields in the DICOM file. The distances $s_1$ and $s_2$ extend from the start point to the contrast bolus front (end point) along the centerline of the vessel (FIG. 3, reference 215 and 217). This can for instance be done by determining the Euclidian distance along the centerline between the two points.

Figure 8:
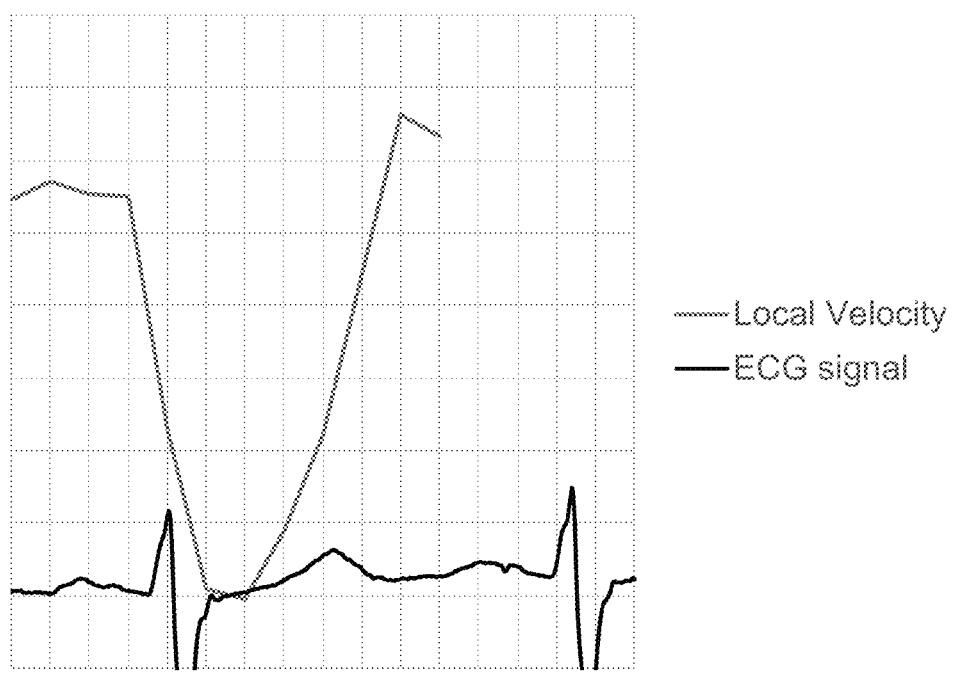
FIG. 8 shows a graph containing all $v_{local}$ values per frame and their matching with the ECG-signal.

Optionally, the distances $s_1$ and $s_2$ can be determined using an automatically detected centerline using vessel detection algorithms as for instance described in Gronenschild et al, "CAAS II: A Second Generation System for Off-line and On-line Quantitative Coronary Angiography", Catheterization and Cardiovascular Diagnosis 33: 61-75 (1994). This creates a more reliable two-dimensional distance measurement along the given input centerline than is the case in a manually defined centerline. In this method the previously (manually) defined centerline is used as an input. Then quantitative analysis based on pixel intensities is performed using the input centerline to determine the segmentation edges of the vessel. The updated centerline is then defined as the center of the detected segmentation edges. The complete subject matter of the publication referenced herein is incorporated by reference herein in its entirety Optionally, it is possible to create a matrix of selected $v_{local}$ values for various combinations of input frames A and B. Such a matrix gives an overview of $v_{local}$ behavior for different selections of frames, and creates insight in how the $v_{local}$ changes when measured over different parts of the cardiac cycle as can be seen in FIG. 7. Plotting in a graph for example all $v_{local}$ values calculated using for instance a single frame difference between frame A and frame B subsequent for all the frames within a full cardiac cycle, represents the velocity change during the cardiac cycle as contrast agent propagates through the target vessel as can be seen in FIG. 8, further known as 'full velocity profile'. FIG. 8 illustrates what can be achieved by this invention; the creation of a full velocity profile as a combination of multiple local velocities ($v_{local}$) within a heart cycle.

The full velocity profile has a patient independent profile shape. One or more profiles were used to create a generic, averaged full velocity profile. In which each full velocity profile was normalized on the basis of the minimum and maximum values of the velocity found.

Furthermore, the ECG signal corresponding to the full velocity profiles are also averaged to create a generic ECG signal.

Figure 10:
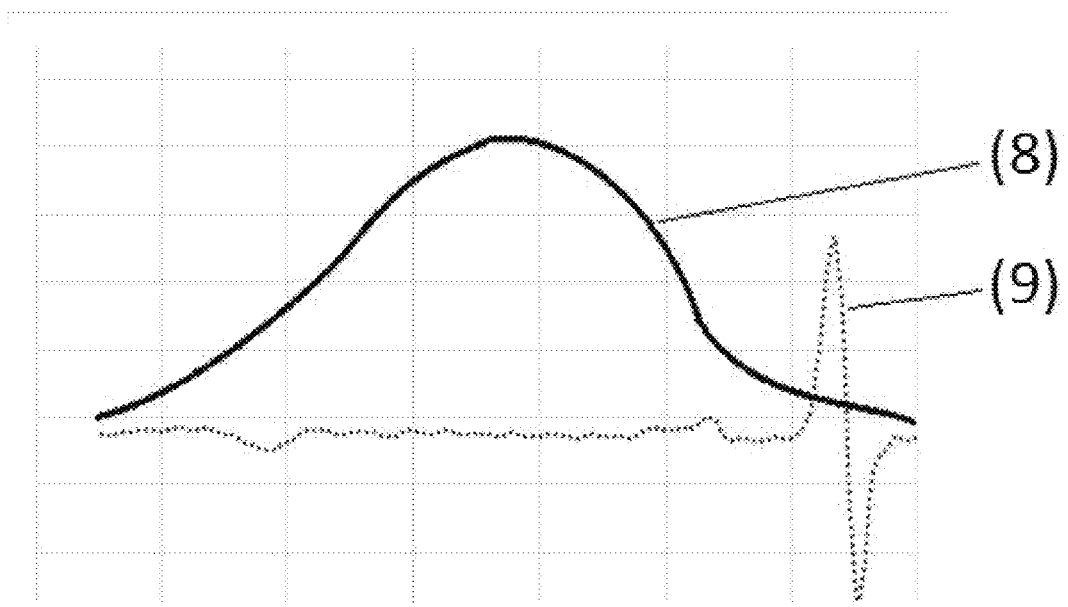
FIG. 10 shows an averaged velocity graph matched to a generic ECG profile.

This results in a generic full profile f(x) (FIG. 10, reference 8) for one heart cycle matched to the generic ECG signal (FIG. 10, reference 9). The heart cycle is advantageously normalized: the start of the heart cycle ("0") corresponds to R peak of the ECG profile while the end of the heart cycle ("1") corresponds to next R peak of the ECG profile.

Optionally these patient independent generic full profiles can be created by preselecting the full profiles that were used to create a generic, averaged full velocity graph based on different coronary vessel tree structures, such as right dominant, left dominant, small right dominant and balanced. These coronary vessel tree difference in relation to the coronary dominant type are in detailed described by Dodge et al, "Lumen diameter of normal human coronary arteries: influence of age, sex, anatomic variation, and left ventricular hypertrophy or dilation", Circulation 1992; 86: 232-246.

Figure 9:
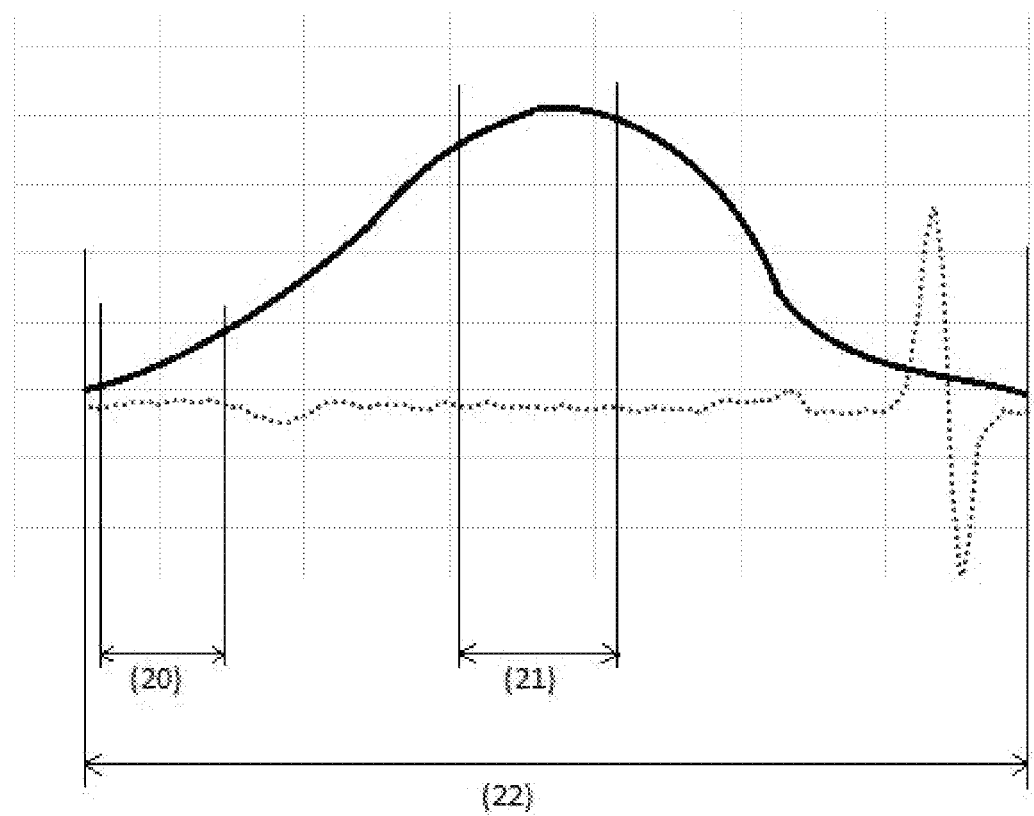
FIG. 9 shows an example of different intervals within one heart cycle.

In case the $v_{local}$ is computed within a part of the cardiac cycle, $v_{local}$ does not represent the average blood velocity for that patient. In this situation the time interval over which the $v_{local}$ value has been determined is dependent on a corresponding section of the heart phase. In different sections of the heart phase the $v_{local}$ value can therefore be an over- or under estimation as related to the average blood velocity of the patient as can be seen in FIG. 9. The $v_{local}$ corresponding to interval (20, within FIG. 9) is for instance different compared to the $v_{local}$ corresponding to interval (21 within FIG. 9). Therefore, the $v_{local}$ needs to be corrected to an average velocity value $v_{mean}$ over an entire heart cycle (22 within FIG. 9). For this translation method (FIG. 1, S5), the generic full velocity profile is used. The full velocity profiles can be obtained from different patients for instance through a database and have corresponding ECG signals.

The generic full velocity profile (f(x)) is a powerful tool in translating the $v_{local}$ to the $v_{mean}$. It is used to calculate a correlation factor $c_f$ for the $v_{local}$ to obtain $v_{mean}$. This correlation factor is based on a normalized integral over the part of the heart cycle covered:

$$c_f = \int_0^1 f(x) \bigg/ \frac{\int_{start}^{end} f(x)}{end - start} \qquad (eq.\ 2)$$

where f(x) represents the generic full velocity profile and start and end are the start and end frame times within the normalized heart cycle [0, 1].

In other words, start and end are the start and end frame times converted to heart phase position of the frames A and B in which $v_{mean}$ needs to be calculated. Note that in case of an ECG gated contrast injection system, the start variable is actually fixed to a certain moment in the normalized heart cycle, simplifying the equation as well as providing more accurate and consistent results.

This conversion is needed to match the input frames to a certain time moment in the generic, normalized velocity profile. This can be done for instance by detecting the R peaks of the QRS complex (see FIG. 11) as taught by Manikandan et al "A novel method for detecting R-peaks in electrocardiogram (ECG") signal", Biomedical Signal Processing and Control 7 (2012) 118-128.

When all the R peaks in an image run are detected, their corresponding frame numbers are known. Therefore, the interval spanned between the start and end frame can be linked to an interval relative to the detected R peaks. The interval between two R peaks is normalized to an interval between 0 and 1, and the interval between the start and end frame is normalized with the same ratio, resulting in an interval relative to the heart phase.

The average velocity $v_{mean}$ can then be calculated as:

$$v_{mean} = \frac{v_{local}}{c_f} \qquad (eq.\ 3)$$

where $v_{local}$ is the velocity measured over the vessel segment between the contrast fronts in the given input frames and $c_f$ is the correlation factor.

An average velocity $v_{mean}$ can also be used to calculate a volumetric flow value Q following the standard equation:

$$Q = v_{mean} \cdot \pi \cdot \left(\frac{d}{2}\right)^2 \qquad (eq.\ 4)$$

where d is the diameter of the vessel in which $v_{mean}$ is calculated.

The diameter of the vessel should correspond to the average diameter over the vessel segment analyzed. To achieve this, the value can be manually set for instance by drawing a line in the two-dimensional angiographic frame.

Alternatively, the average diameter can also be detected automatically, for example by the detection algorithms described in U.S. Pat. No. 8,787,641. For this detection algorithm, the centerline used as input in S3, 205, 207 can be used as an input. This redefines the centerline, but as it also detects vessel borders, it can also be used to create a diameter graph along the centerline. Of such graph, an average diameter can be derived. The complete subject matter of the patent referenced herein is incorporated by reference herein in its entirety.

The embodiment is not dependent on the temporal resolution ($t_{cineframe}$) as defined by the image cine frame rate (which might be limited to 7.5 frames per second), but only by the temporal resolution of the shutter of the imaging system ($t_{acquisition}$), which lies considerably higher usually around 20 milliseconds.

Several possible variations on the embodiment as described above can be defined. These variations are added to the normal flow as described above in FIG. 1 or 3. The variations can be applied separately from each other, or together as multiples. A more detailed description of each variation is described below.

Optionally, a 3D model may be used for correction of two-dimensional distances. In this case, one or multiple 3D models mapped to the two-dimensional centerlines available in the start and the end frame needs to be available.

Instead of measuring two-dimensional distances along the centerlines (for instance Euclidian distances), 3D distances in the 3D model from and to the corresponding mapped two-dimensional points are calculated, allowing a better distance estimation.

To do this, a match has to be established between the 3D model and the angiographic image run. First, the 3D model is positioned such that the patient position is equal to the patient position of the image run. Preferably, a frame of the image run is chosen wherein the heart phase of the frame is matched to that of the 3D model. If for instance, the 3D model is derived from CT data, the data is recorded during one specific moment within the heart phase, whereas the two-dimensional image run contains multiple heart phases. Aligning the heart phase ensures a better matching.

The 3D model is then back projected onto the chosen two-dimensional frame as taught by for instance Lay, "Linear algebra and its applications", 2012, 4th edition, p. 142-143, Addison-Wesley Longman. This can be done using a 3D centerline model or a 3D lumen model. The complete subject matter of the publication referenced herein is incorporated by reference herein in its entirety.

To simplify the matching of the back projected 3D model to the two-dimensional frame, the lumen in the two-dimensional frame is emphasized. This can be done using a vesselness filter which takes into account the diameters of the lumen that need to be found in the image, for instance Frangi, "Multiscale vessel enhancement filtering", In Medical Image Computing and Computer-Assisted Intervention—MICCAI 1998, Lecture Notes in Computer Science, Vol 1496 pp 130-137. The complete subject matter of the publication referenced herein is incorporated by reference herein in its entirety. These diameters can be retrieved directly from the 3D model in case of a lumen-model. When only the centerline is extracted an educated guess of the corresponding diameters can be made using literature about the diameters Dodge et al, "Lumen diameter of normal human coronary arteries: influence of age, sex, anatomic variation, and left ventricular hypertrophy or dilation", Circulation, 1992: 82: 232-246. This results in a two-dimensional vesselness image. The complete subject matter of the publication referenced herein is incorporated by reference herein in its entirety.

The matching between the two-dimensional computed vesselness image and the back projected 3D model is performed by calculating the costs of the mismatch between the back projected 3D centerline model and the two-dimensional vesselness centerlines. For every back projected 3D point, a cost is determined. This cost is for instance the Euclidian distance to the nearest-neighbor point. The total cost for the match between this back projected 3D centerline model and the two-dimensional vesselness image is a summation of the cost for all points of the back projected 3D centerline model.

The minimum cost represents the best match between the back projected 3D model and the two-dimensional frame. Using this match, the 3D centerline can be used to correct the two-dimensional distance between the two-dimensional points.

In addition to calculating an average velocity $v_{mean}$ in a vessel of interest, the velocity in other parts of the same vessel tree can be calculated, granting access to velocity in vessels even if not properly visible in angiography or part of a 3D model.

This is done by indicating one or more vessel segments of interest (SOI) in (part of) the vessel tree of the patient as well as indicating the segment of the vessel tree that corresponds to $v_{mean}$. The (part of) the vessel tree can for instance be indicated in a generic vessel tree retrieved from a database, preferably corresponding to the heart type of the patient or, if available, for instance a patient-specific CT scan.

The vessel segment belonging to $v_{mean}$ can be indicated manually by the user in (part of) the vessel tree or can be determined automatically. When an annotated 3D model (containing labels for each vessel segment) is available of part or all of the vessel tree, the vessel segment belonging to $v_{mean}$ can be determined by back projecting the 3D model onto the two-dimensional angiographic image as described above.

Once the vessel segment belonging to $v_{mean}$ is known, propagation of the velocities can be done. As every patient has a heart type which can be determined to be either right dominant, left dominant, small right dominant or balanced as can be seen in FIG. 10, based on this heart type every patient has a specific coronary vessel tree with specific relative diameters in the coronary vessel tree as described by Dodge et al, "Lumen Diameter of Normal Human Coronary Arteries. Influence of age, sex, anatomic variation, and left ventricular hypertrophy or dilation", Circulation, Vol 86, No 1, 232-246 (1992).

Scaling laws then combine diameters for a certain heart type before and after a bifurcation in the vessel tree with a given input velocity to calculate velocity and flow on the other two branches of the bifurcation as described in Huo et al., "Intraspecific scaling laws of vascular trees", J. R. Soc. Interface (2012) 9, 190-200. The complete subject matter of the publication referenced herein is incorporated by reference herein in its entirety.

Combining Murray's scaling Law and the preservation of flow $Q_p = Q_{d1} + \ldots + Q_{dN}$, that is proximal flow is equal to the sum of the distal flows. For a bifurcation this equals:

$$Q_p = Q_{d1}\left(1 + \left(\frac{r_{d2}}{r_{d1}}\right)^3\right) \qquad \text{(eq. 5)}$$

where $r_{d2}$ and $r_{d1}$ are the radius of the two distal vessels. Using the diameters of the generic heart models, it is possible to calculate any velocity value through the entire vessel tree. This creates an extra processing step after step S6 of FIG. 3.

Optionally image registration can be performed on input angiographic subtraction image frames as an extra processing step in operation S2 of FIG. 3. This simplifies centerline extraction and distance calculation, in particular when the goal is to create a velocity matrix as described in FIG. 7.

Instead of determining multiple intensity profiles (one for each frame as shown in FIG. 6, reference 6), an alternative approach is possible in which a single cumulative intensity profile along the vessel is created. For this approach image registration for every frame of the image run is required. Image registration during contrast injection is complex, therefore an alternative approach is used. In this approach as for instance taught by Fischer, B., Bommersheim, S., "Non-rigid image registration", In: http://www.mic.uni-luebeck.de/uploads/tx_wapublications/2006-KOREA-BF.pdf, 2006 non-rigid image registration is performed in a heart cycle after contrast injection. Heart motion is linked directly to the heart cycle. If a blood vessel has been registered for an entire heart cycle after total perfusion of the vessel, the found registration can be mapped back to one or more heart cycles that lie before contrast has entirely perfused the vessel of interest and in which direct registration was impossible. The complete subject matter of the publication referenced herein is incorporated by reference herein in its entirety.

Figure 12:
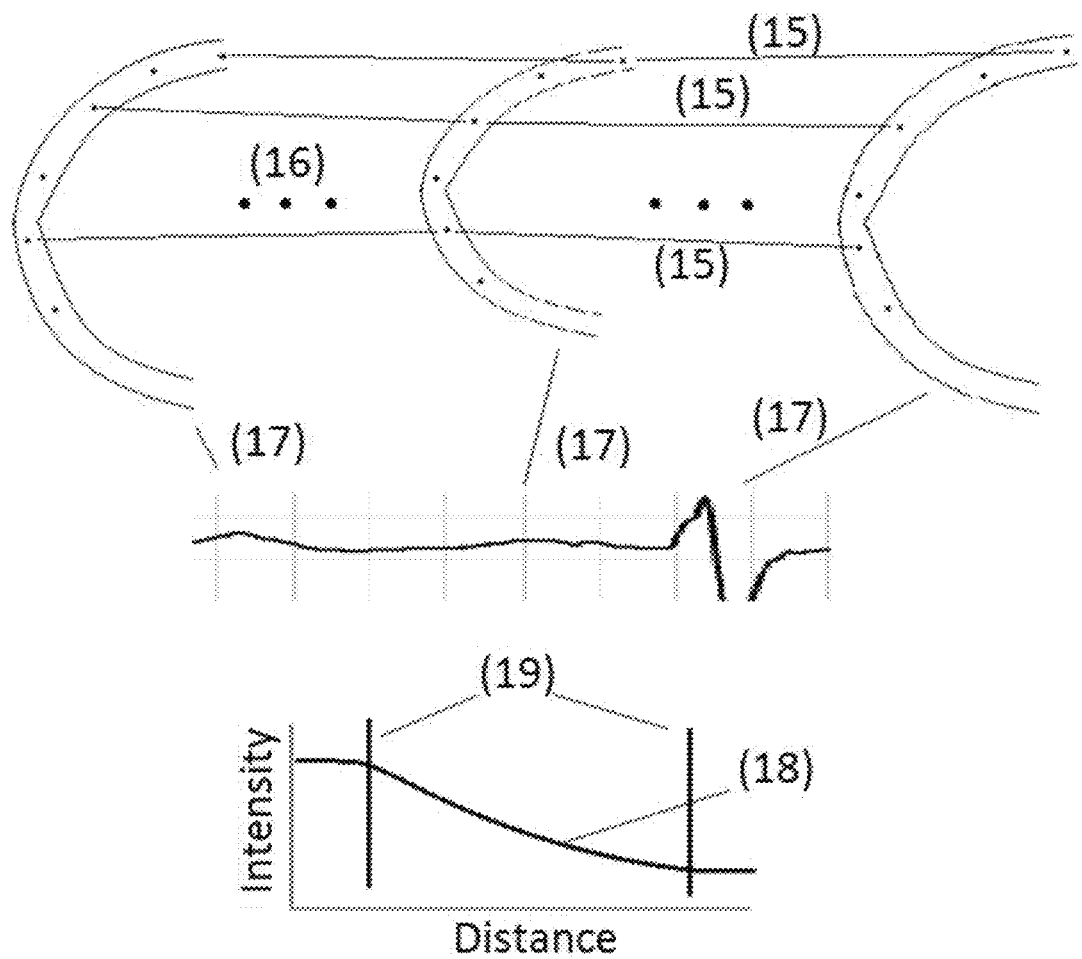
FIG. 12 shows an example of an alternative method to determine velocity based on centerline tracking through a heart cycle.

Every frame (FIG. 12, reference 16) in the fully visible vessel tree is mapped to a moment in the heart cycle linked to the ECG signal (FIG. 12, reference 17), and the same is done during contrast propagation. Then, a fixed number of centerline points is registered along all frames (FIG. 12, reference 15). These centerline points correspond to the x-axis on a new intensity graph (FIG. 6). The y intensity values of this graph are acquired by cumulatively adding the pixel values of the registered centerline points and a small area around them to get a value. This results in a different intensity curve following the propagation of contrast agent through the vessel of interest (FIG. 12, reference 18). Based on this new intensity curve, a cutoff point for contrast start and end in the cumulative time interval can be determined (FIG. 12, reference 19) to calculate the distance and thus the velocity in between, using the calculations as previously defined.

Alternatively, this intensity curve can be used as a guidance for the user when using the calculation method of (eq. 1) to select frame A and frame B in which the contrast bolus front must be visible.

Furthermore, in case of image registration, the start point (which is registered over time in all possible frames of the image run) may be used to determine the moment of contrast injection in the vessel tree by identifying the frame with maximal contrast intensity at the start point in the image run. This can be used as a suggestion for frame A.

When image registration is used as described above, this can also be used as a further alternative method to determine identical start points in frame A and frame B by matching the first centerline point in frame A to a registered point in frame B (or vice versa).

Instead of using a velocity correlation method to calculate the $v_{mean}$, there are alternative methods to get to a $v_{mean}$. The main objective of such alternative method is to identify the part of the heart phase in which the velocity is measured. The aim is to measure along a set part of the heart cycle, so the $v_{local}$ obtained has a fixed correlation factor to get to the $v_{mean}$.

One approach for instance covers the maximal velocity during a heart cycle by measuring the velocity when the velocity graph is at its peak (FIG. 11, reference 13), which makes drawing and detection of the velocity at this area easier. For instance, for the right coronary artery this means measuring the velocity from the P-wave of a heart cycle to the T-wave of the heart cycle as can be seen in FIG. 11. By detecting the P-wave and the T-wave (FIG. 11, reference 14) of the input ECG matching with the input angiographic image, it is possible to identify frames in the image run corresponding to the P and T-wave. The identification of the T and the P-wave can be either done manually by the user, of automatically detected, for example as described by Mehta, S. S., Lingayat, N.S., "Detection of P and T-waves in Electrocardiogram", In: Proceedings of the World Congress on Engineering and Computer Science 2008, who use slope detection to identify and filter out first a QRS complex from an ECG signal, followed by using the same technique to detect and filter out the slighter slopes of first the T-wave and finally the P-wave. The frames corresponding to the T-wave and P-wave peaks must be used as start and end frames A and B for velocity calculations. This changes (eq. 1) to the following equation for $v_{local}$.

$$v_{local} = \frac{s_{twave} - s_{pwave}}{t_{twave} - t_{pwave}} \qquad \text{(eq. 6)}$$

where $v_{local}$ is the velocity measured over the vessel segment between the contrast fronts in the given input frames,
$s_{twave}$ the distance measured in the frame corresponding to the T-wave,
$s_{pwave}$ the distance measured in the frame corresponding to the P-wave,
$t_{twave}$ the timestamp of acquisition of the frame corresponding to the T-wave, and
$t_{pwave}$ the timestamp of acquisition of the frame corresponding to the P-wave.

It should be noted that the application of an ECG gated contrast injection can also make this process more reliable, as it ascertains contrast injection will not take place in this moment of measurement, and is always a set time before the determination of this version of $v_{local}$.

Furthermore, as the interval is constant, (eq. 2) is not needed anymore. Instead of this equation, $c_f$ is equal to a constant value $C_f$, which can be used to calculate average $v_{mean}$ as described in (eq. 3):

$$v_{mean} = \frac{v_{local}}{c_f} \qquad \text{(eq. 7)}$$

where $v_{local}$ is the velocity measured over the vessel segment between the contrast fronts in the given input frames and $c_f$ is the constant correlation factor.

Alternatively, another method to calculate $v_{mean}$ is based on measuring the velocity along one cardiac heart cycle. By mapping the heart cycles to an ECG graph as described above, it is possible to determine the length of the heart cycle measured in number of frames. Once the number of frames between the start frame and the end frame is equal to one heart cycle, the correlation factor $c_f$ becomes equal to one, and hence it is possible to state that:

$$v_{mean} = v_{local} = \frac{s_2 - s_1}{t_2 - t_1} \qquad \text{(eq. 8)}$$

In case two-dimensional angiographic image runs do not have an ECG graph available, or have a highly irregular or noisy ECG signal, the embodiment can be adjusted in such a manner that it is still possible to correct the velocity and obtain the true $v_{mean}$. This approach requires a more extensive analysis to compensate for the fact that no ECG signal is available to give initial guidance to the part of the heart phase being analyzed. For this, it is required to analyze all available image frames between the 'start' frame A and the 'end' frame B. The method requires a velocity matrix and derived from this a velocity graph to be created (FIG. 7 and FIG. 8). A velocity graph v(x) with an interval time of a single frame per measured point gives a profile not unlike the generic profile $v_{gen}(x)$ as seen in FIG. 10. By fitting v(x) to $v_{gen}(x)$, it is possible to determine which part of the heart cycle corresponds to v(x). Once this is known, it is possible to use (eq. 2) and (eq. 3) to establish the true velocity $v_{mean}$, and after this the volumetric flow Q using (eq. 4).

The average velocity $v_{mean}$ as computed above over a heart cycle can be the starting point of further calculations and estimations, such as for instance coronary flow reserve (CFR) or computational fluid dynamics (CFD) calculations for instance to assess wall shear stress or pressure drop within the conduit.

Optionally, the translation of the $v_{local}$ to $v_{mean}$ (operation S5 of FIG. 1) can be omitted. In this case, $v_{mean}$ is equal to $v_{local}$ for all further calculations.

The embodiment described herein can be used on a standalone system or included directly in, for instance, an x-ray fluorographic system or any other image system to acquire two dimensional angiographic images. FIG. 17 illustrates an example of a high-level block diagram of an x-ray cinefluorograpic system. In this block diagram the embodiment is included as an example how the embodiment could integrate in such system.

Portions of the system (as defined by various functional blocks) may be implemented with dedicated hardware, analog and/or digital circuitry, and/or one or more processors operating program instructions stored in memory.

Figure 13:
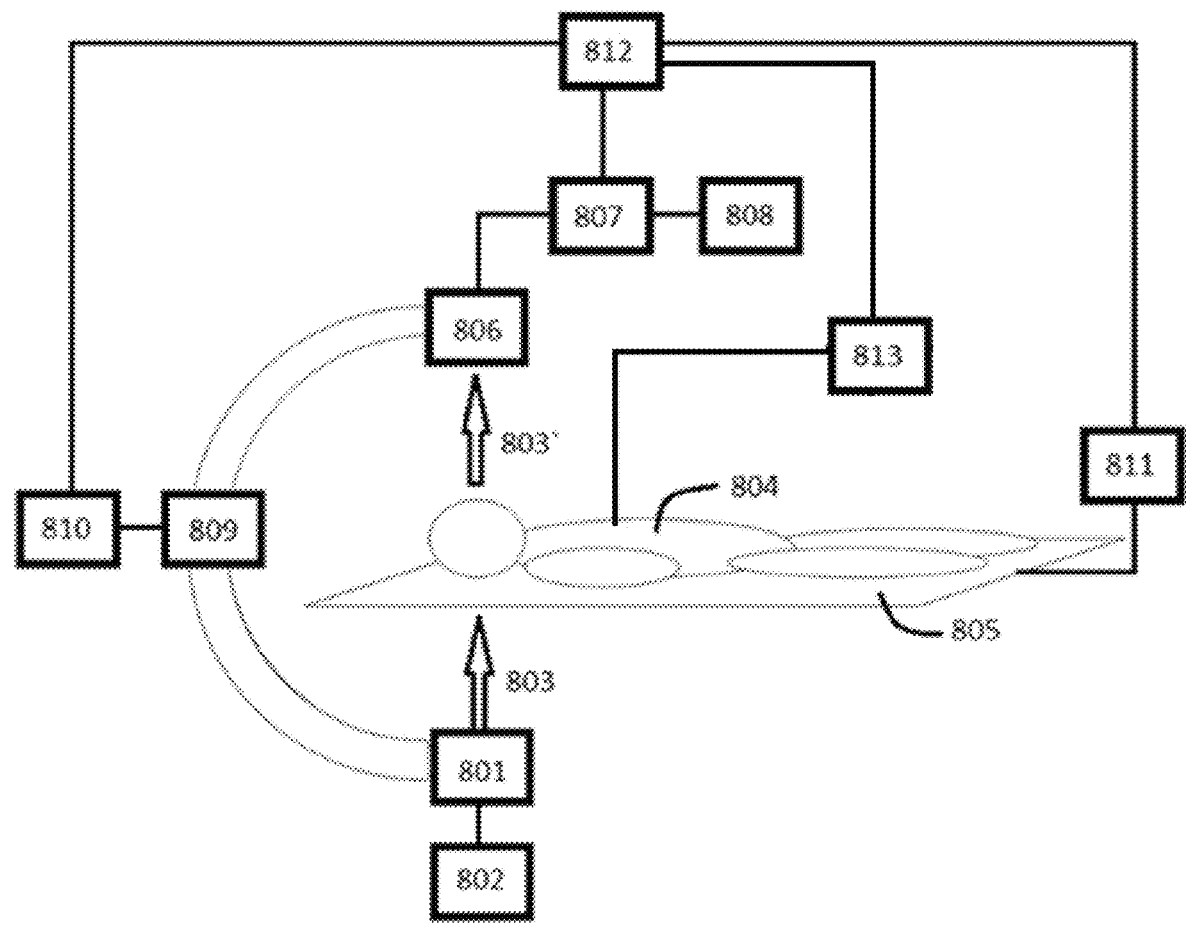
FIG. 13 shows a functional block diagram of an exemplary single plane angiographic system.

The X-ray system of FIG. 13 includes an X-ray tubes 801 with a high voltage generator 802 that generates an X-ray beam 803.

The high voltage generator 802 controls and delivers power to the X-ray tube 801. The high voltage generator 802 applies a high voltage across the vacuum gap between the cathode and the rotating anode of the X-ray tube 801.

Due to the voltage applied to the X-ray tube 801, electron transfer occurs from the cathode to the anode of the X-ray tube 801 resulting in X-ray photon-generating effect also called Bremsstrahlung. The generated photons form an X-ray beam 803 directed to the image detector 806.

An X-ray beam 803 consists of photons with a spectrum of energies that range up to a maximum determined by among others the voltage and current submitted to the X-ray tube 801.

The X-ray beam 803 then passes through the patient 804 that lies on an adjustable table 805. The X-ray photons of the X-ray beam 803 penetrate the tissue of the patient to a varying degree. Different structures in the patient 804 absorb different fractions of the radiation, modulating the beam intensity.

The modulated X-ray beam 803' that exits from the patient 804 is detected by the image detector 806 that is located opposite of the X-ray tube. This image detector 806 can either be an indirect or a direct detection system.

In case of an indirect detection system, the image detector 806 consists of a vacuum tube (the X-ray image intensifier) that converts the X-ray exit beam 803' into an amplified visible light image. This amplified visible light image is then transmitted to a visible light image receptor such as a digital video camera for image display and recording. This results in a digital image signal.

In case of a direct detection system, the image detector 806 consists of a flat panel detector. The flat panel detector directly converts the X-ray exit beam 803' into a digital image signal.

The digital image signal resulting from the image detector 806 is passed through a digital image processing unit 807. The digital image processing unit 807 converts the digital image signal from 806 into a corrected X-ray image (for instance inverted and/or contrast enhanced) in a standard image file format for instance DICOM. The corrected X-ray image can then be stored on a hard drive 808.

Furthermore, the X-ray system of FIG. 13 consists of a C-arm 809. The C-arm holds the X-ray tube 801 and the image detector 806 in such a manner that the patient 804 and the adjustable table 805 lie between the X-ray tube 801 and the image detector 806. The C-arm can be moved (rotated and angulated) to a desired position to acquire a certain projection in a controlled manner using the C-arm control 810. The C-arm control allows for manual or automatic input for adjustment of the C-arm in the desired position for the X-ray recording at a certain projection.

The X-ray system of FIG. 13 can either be a single plane or a bi-plane imaging system. In case of a bi-plane imaging system, multiple C-arms 809 are present each consisting of an X-ray tube 801, an image detector 806 and a C-arm control 810.

Additionally, the adjustable table 805 can be moved using the table control 811. The adjustable table 805 can be moved along the x, y and z axis as well as tilted around a certain point.

A general unit 812 is also present in the X-ray system. This general unit 812 can be used to interact with the C-arm control 810, the table control 811 and the digital image processing unit 807.

The injection of contrast agent is done using a contrast injector 813. The contrast injector 813 can be ECG gated and controlled by the general unit 812 or controlled upon user input.

An embodiment is implemented by the X-ray system of FIG. 13 as follows. A clinician or other user acquires an X-ray angiographic image of a patient 804 at a certain projection by using the C-arm control 810 to move the C-arm 809 to a desired position relative to the patient 804. The patient 804 lies on the adjustable table 805 that has been moved by the user to a certain position using the table control 811.

The sequence of X-ray image frames is then generated using the high voltage generator 802, the X-ray tube 801, the image detector 806 and the digital image processing unit 807 as described above. These image frames are then stored on the hard drive 808 or a server. Using this X-ray image frames, the general processing unit 812 calculate local velocities or the average velocity by performing one or more of the operations disclosed above with reference to FIGS. 1 and 3 and related variants and combinations. Such velocities can also be calculated by a processing system having access to the hard drive or the server. The system comprises memory configured to read a sequence of contrast enhanced image frames of a target conduit, typically a vessel and, one or more processors that, when executing program instructions stored in the memory, are configured to perform the method according to embodiments herein, particularly the operations as disclosed with reference to FIGS. 1 and 3 and related variants and combinations.

There have been described and illustrated herein several embodiments of a method and apparatus for determining optimal image viewing direction in terms of reduced foreshortening and relevancy of information. While particular embodiments have been described, it is not intended that the invention be limited thereto, as it is intended that the invention be as broad in scope as the art will allow and that the specification be read likewise. For example, the data processing operations can be performed offline on images stored in digital storage, such as a picture archiving and communication system (PACS) commonly used in the medical imaging arts. It will therefore be appreciated by those skilled in the art that yet other modifications could be made to the provided embodiments without deviating from its spirit and scope as claimed.

The embodiments described herein may include a variety of data stores and other memory and storage media as discussed above. These can reside in a variety of locations, for instance as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). The system may also include one or more storage devices, for instance as disk drives, optical storage devices and solid-state storage devices such as random-access memory ("RAM") or read-only memory ("ROM"), as well as removable media devices, memory cards, flash cards, etc.

The devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

Certain embodiments as described herein can include logic or a number of components, modules, or mechanisms. Modules may constitute either software modules (e.g., code embodied (1) on a non-transitory machine-readable medium or (2) in a transmission signal) or hardware-implemented modules. A hardware-implemented module is tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired) or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules may provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs)).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program may be written in any form of programming language, including compiled or interpreted languages, and it may be deployed in any form, including as a stand-alone program or as a module, subroutine, or other unit suitable for use in a computing environment. A computer program may be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations may also be performed by, and apparatus of example embodiments may be implemented as, special purpose logic circuitry, e.g., a field programmable gate array (FPGA) or an application-specific integrated circuit (ASIC).

The computing system may include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 14:
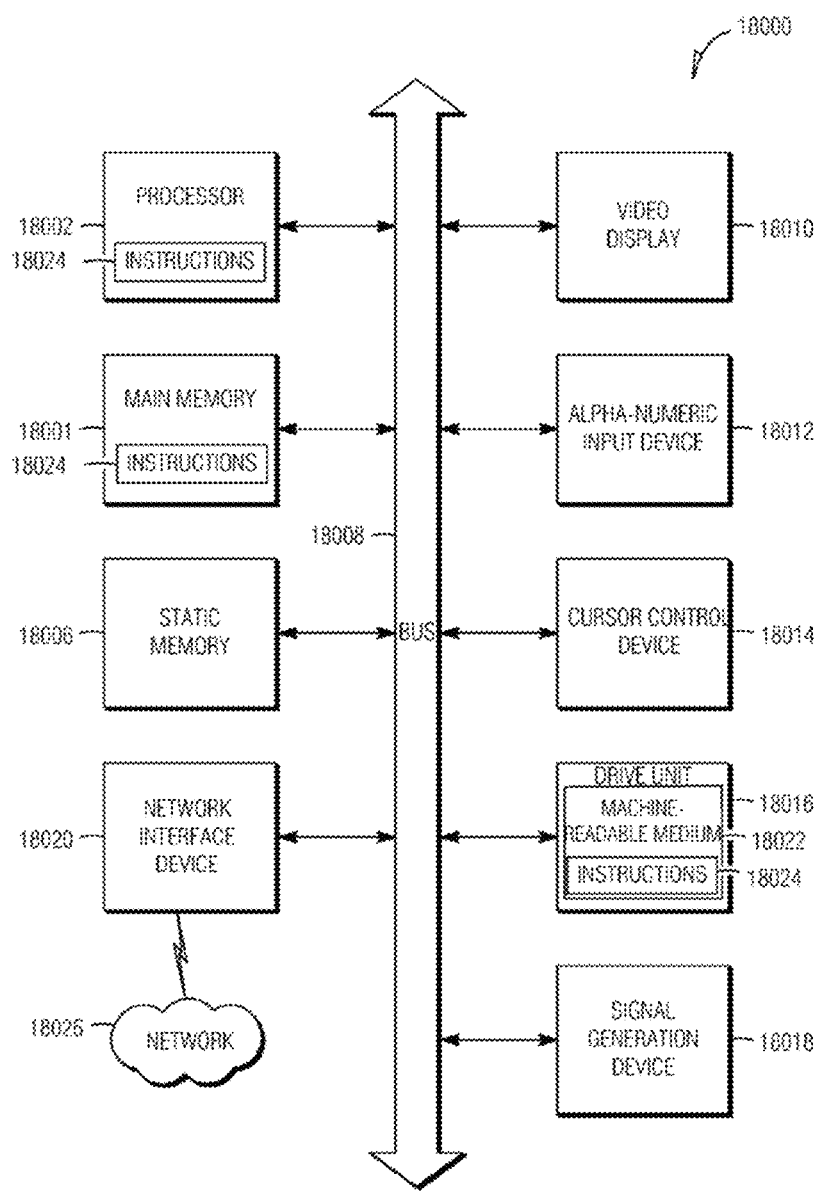
FIG. 14 shows an example computer system.

FIG. 14 shows a diagrammatic representation of a machine in the example form of a computer system 18000 within which a set of instructions for causing the machine to perform any one or more of the methods, processes, operations, or methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a Personal Computer (PC), a tablet PC, a Personal Digital Assistant (PDA), a cellular telephone or smartphone, a Web appliance, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Example embodiments may also be practiced in distributed system environments where local and remote computer systems which that are linked (e.g., either by hardwired, wireless, or a combination of hardwired and wireless connections) through a network, both perform tasks. In a distributed system environment, program modules may be located in both local and remote memory-storage devices (see below).

The example computer system 18000 includes a processor 18002 (e.g., a Central Processing Unit (CPU), a Graphics Processing Unit (GPU) or both), a main memory 18001 and a static memory 18006, which communicate with each other via a bus 18008. The computer system 18000 may further include a video display unit 18010 (e.g., a Liquid Crystal Display (LCD) or a Cathode Ray Tube (CRT)). The computer system 18000 also includes an alphanumeric input device 18012 (e.g., a keyboard), a User Interface (UI) cursor controller 18014 (e.g., a mouse), a disk drive unit 18016, a signal generation device 18018 (e.g., a speaker) and a network interface device 18020 (e.g., a transmitter).

The disk drive unit 18016 includes a machine-readable medium 18022 on which is stored one or more sets of instructions 18024 and data structures (e.g., software) embodying or used by one or more of the methodologies or functions illustrated herein. The software may also reside, completely or at least partially, within the main memory 18001 and/or within the processor 18002 during execution thereof by the computer system 18000, the main memory 18001 and the processor 18002 also constituting machine-readable media.

The instructions 18024 may further be transmitted or received over a network 18026 via the network interface device 18020 using any one of a number of well-known transfer protocols (e.g., HTTP, Session Initiation Protocol (SIP)).

The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform any of the one or more of the methodologies illustrated herein. The term "machine-readable medium" shall accordingly be taken to include, but not be limited to, solid-state memories, and optical and magnetic medium.

Method embodiments illustrated herein may be computer-implemented. Some embodiments may include computer-readable media encoded with a computer program (e.g., software), which includes instructions operable to cause an electronic device to perform methods of various embodiments. A software implementation (or computer-implemented method) may include microcode, assembly language code, or a higher-level language code, which further may include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, Random Access Memories (RAMs), Read Only Memories (ROMs), and the like.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ the variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A computer-implemented method for quantitative flow analysis of blood flowing in a blood vessel from a sequence of two-dimensional image frames of such blood vessel covering one or more heart cycles, which such image frames are timely separated by a certain time interval, the method employing a processor having processor-executable instructions to perform operations comprising:
   a) selecting a pair of two-dimensional image frames from the sequence of two-dimensional image frames, wherein the pair of two-dimensional image frames consists of a start image frame and an end image frame where contrast agent is present in the blood vessel;
   b) determining a centerline of the blood vessel in the start image frame;
   c) determining a centerline of the blood vessel in the end image frame;

d) identifying a common start point on the centerline of the start image frame and on the centerline of the end image frame, wherein the common start point is based on image processing operations that determine location of an infusion catheter tip or location of an anatomical reference point in both the start image frame and the end image frame;

e) identifying an end point on the centerline of the start image frame, wherein the end point for the start image frame corresponds to location of a front of the contrast agent in the blood vessel distal to the common start point in the start image frame, wherein the location of the front of the contrast agent in the blood vessel in the start image frame is based on image processing operations that determine the location of the front of the contrast agent in the blood vessel in the start image frame;

f) identifying an end point on the centerline of the end image frame, wherein the end point for the end image frame corresponds to location of the front of the contrast agent in the blood vessel distal to the common start point in the end image frame, wherein the location of the front of the contrast agent in the blood vessel in the end image frame is based on image processing operations that determine the location of the front of the contrast agent in the blood vessel in the end image frame;

g) calculating a first centerline distance between the start point and the end point of the start image frame;

h) calculating a second centerline distance between the start point and the end point of the end image frame;

i) calculating a local flow velocity of blood within the blood vessel for part of a heart cycle as a function of the first and second centerline distances of g) and h) and a time interval between the start image frame and the end image frame;

j) using a correlation factor to adjust the local flow velocity of i) to determine an average flow velocity of blood within the blood vessel for one entire heart cycle; and k) displaying information to a user, wherein the information characterizes blood flow in the blood vessel, and wherein the information is based on at least one of the local flow velocity of i) and the average flow velocity of j).

2. The method according to claim 1, wherein the sequence of two-dimensional image frames contains information for determining the distribution over time of a contrast agent travelling in the blood vessel, and the start image frame and the end image frame relate to different distributions of the contrast agent in the blood vessel from a proximal point to distal points located on the centerlines of the start image frame and the end image frame.

3. The method according to claim 1, further comprising an ECG gated contrast injection phase, the start image frame being identified by an image frame in which the ECG gated contrast injection phase starts or ends.

4. The method according to claim 1, wherein the image processing operations of e) and f) comprise calculating intensity versus centerline distance graphs from the common start point in the start image frame and the end image frame, respectively, the end point in either the start image frame or the end image frame being identified by setting a threshold and identifying the centerline distance corresponding to the point having intensity equal to such threshold.

5. The method according to claim 1, wherein the sequence of two-dimensional image frames contains digitally subtracted image frames, or the operations further comprise digitally subtracting the two-dimensional image frames of the sequence from a mask frame or multiple mask frames to obtain digitally subtracted image frames to enhance the flow in the blood vessel.

6. The method according to claim 1, wherein the operations further comprise calculating at least one additional local flow velocity within the blood vessel based on different image frame pair selection to determine local flow velocities within the blood vessel as a function of time, and wherein the information displayed in k) is based on the local flow velocities within the blood vessel as a function of time.

7. The method according to claim 6, wherein the operations further comprise using the local flow velocities within the blood vessel as a function of time for further quantitative processing of the blood vessel.

8. The method according to claim 7, wherein the further quantitative processing of the blood vessel involves volumetric flow analysis, CFR, CFD or the like calculations.

9. The method according to claim 6, wherein the operations further comprise using the local flow velocities within the blood vessel as a function of time to determine an average velocity within the blood vessel over a heart cycle, and wherein the information displayed in k) is based on the average velocity within the blood vessel over the heart cycle.

10. The method according to claim 9, wherein the operations further comprise using the average velocity within the blood vessel over the heart cycle for further quantitative processing of the blood vessel.

11. The method according to claim 10, wherein the further quantitative processing of the blood vessel involves volumetric flow analysis, CFR, CFD or the like calculations.

12. The method according to claim 6, wherein the information displayed in k) represents local flow velocities within the blood vessel over a heart cycle.

13. The method according to claim 6, wherein the information displayed in k) represents local flow velocities within the blood vessel over a heart cycle and an ECG signal over the heart cycle.

14. The method according to claim 1, wherein the correlation factor of j) is derived from velocity profiles and corresponding ECG signals obtained from a plurality of different patients.

15. The method according to claim 14, wherein the correlation factor of j) is based on a normalized integral over the image frames covering one or more heart cycles according to $$c_f = \int_0^1 f(x) \bigg/ \frac{\int_{start}^{end} f(x)}{end - start}$$

where f(x) represents a generic full velocity profile and start and end are the start and end image frame times related to the generic full velocity profile.

16. The method according to claim 14, wherein the operations further comprise propagating the average velocity within the blood vessel to other segments of the blood vessel to estimate average velocity in such other segments.

17. The method according to claim 1, wherein the correlation factor of j) is calculated by processing an input database of known velocity profiles for one heart cycle.

18. The method according to claim 1, wherein the operations further comprise propagating the local flow velocity within the blood vessel to other segments of the blood vessel to estimate local flow velocity in such other segments.

19. A non-transitory computer-readable medium loadable into memory of a digital computer and comprising software code portions for performing the method according to claim 1 when the software code portions are executed on the digital computer.

20. The method according to claim 1, further comprising receiving user input for the selection of the pair of two-dimensional image frames consisting of the start image frame and the end image frame.

21. The method according to claim 1, wherein the information displayed in k) represents the average flow velocity of blood within the blood vessel over the heart cycle and an ECG signal over the heart cycle.

22. The method according to claim 1, wherein the information displayed in k) represents a volumetric flow value derived from the average flow velocity of j) and size of the blood vessel.

23. An imaging device for acquiring a contrast-enhanced sequence of two-dimensional image frames, the imaging device comprising an acquisition module for obtaining a plurality of two-dimensional image frames of a blood vessel perfused by a contrast agent, a timing module for driving the acquisition module to obtain the sequence of two-dimensional image frames after a trigger event, and a selection module for selecting a pair of two-dimensional image frames from the sequence of two-dimensional image frames, wherein the pair of two-dimensional image frames consists of a start image frame and an end image frame where contrast agent is present in the blood vessel, the device further comprising a processor programmed to:
   a) determine a centerline of the blood vessel in the start image frame;
   b) determine a centerline of the blood vessel in the end image frame;
   c) identify a common start point on the centerline of the start image frame and on the centerline of the end image frame, wherein the common start point is based on image processing operations that determine location of an infusion catheter tip or location of an anatomical reference point in both the start image frame and the end image frame;
   d) identify an end point on the centerline of the start image frame, wherein the end point for the start image frame corresponds to location of a front of the contrast agent distal to the common start point in the start image frame, wherein the location of the front of the contrast agent in the blood vessel in the start image frame is based on image processing operations that determine the location of the front of the contrast agent in the blood vessel in the start image frame;
   e) identify an end point on the centerline of the end image frame, wherein the end point for the end image frame corresponds to location of the front of the contrast agent distal to the common start point in the end image frame, wherein the location of the front of the contrast agent in the blood vessel in the end image frame is based on image processing operations that determine the location of the front of the contrast agent in the blood vessel in the end image frame;
   f) calculate a first centerline distance between the start point and the end point of the start image frame;
   g) calculate a second centerline distance between the start point and the end point of the end image frame;
   h) calculate a local flow velocity of blood within the blood vessel for part of a heart cycle as a function of the first and second centerline distances of f) and g) and a time interval between the start image frame and the end image frame; and
   i) using a correlation factor to adjust the local flow velocity of h) to determine an average flow velocity of blood within the blood vessel for one entire heart cycle; and
   j) displaying information to a user, wherein the information characterizes blood flow in the blood vessel, and wherein the information is based on at least one of the local flow velocity of h) and the average flow velocity of i).

24. The imaging device according to claim 23, wherein the anatomical reference point comprises a point of a vessel bifurcation.

25. The imaging device according to claim 23, wherein the image processing operations of d) and e) involve automatically detecting a drop point in a graph representing intensity versus centerline distance from the common start point.

26. The imaging device according to claim 23, further comprising a digital subtraction angiography module configured to compute a mask frame and subtract such a mask frame or multiple mask frames from the image frames to obtain a sequence of flow-enhanced frames.

27. The imaging device according to claim 23, further comprising an ECG module configured to synchronize acquisition with one or more heart cycles, the processor being configured to calculate local velocities within the vessel for a plurality of couples of image frames of the sequence related to one or more heart cycles.

28. The imaging device according to claim 27, further comprising a contrast injector interfaced with the ECG module to perform contrast injection at a predefined moment within a heart cycle.

29. The imaging device according to claim 28, wherein the contrast injector is configured to inject contrast at the moment of minimal coronary flow.

30. The imaging device according to claim 28, wherein the identification of the start image frame is performed by selecting an image frame in which the ECG gated contrast injection starts.

31. The imaging device according to claim 28, wherein the identification of the start image frame is performed by selecting an image frame in which the ECG gated contrast injection finalizes.

32. The imaging device according to claim 23, wherein the processor is further configured to use the local flow velocity within the blood vessel for further quantitative processing of the vessel.

33. The imaging device according to claim 32, wherein the further quantitative processing of the vessel involves volumetric flow analysis, CFR, CFD or the like calculations.

34. The imaging device according to claim 23, wherein the selection module is configured to receive user input for the selection of the pair of two-dimensional image frames consisting of the start image frame and the end image frame, or the selection module is configured to automatically select the pair of two-dimensional image frames consisting of the start image frame and the end image frame without user input.

35. The imaging device according to claim 23, wherein the processor is further configured to calculate at least one additional local flow velocity within the blood vessel based on different image frame pair selection to determine local flow velocities within the blood vessel as a function of time.

36. The imaging device according to claim 35, wherein the processor is further configured to use the local flow velocities within the blood vessel as a function of time for further quantitative processing of the blood vessel.

37. The imaging device according to claim 36, wherein the further quantitative processing of the vessel involves volumetric flow analysis, CFR, CFD or the like calculations.

38. The imaging device according to claim 35, wherein the processor is further configured to use the local flow velocities within the blood vessel as a function of time to determine an average velocity within the blood vessel over a heart cycle.

39. The imaging device according to claim 38, wherein the processor is further configured to use the average velocity within the blood vessel over a heart cycle for further quantitative processing of the blood vessel.

40. The imaging device according to claim 39, wherein the further quantitative processing of the blood vessel involves volumetric flow analysis, CFR, CFD or the like calculations.

41. The imaging device of claim 23, wherein the information displayed to the user represents at least one of: the average flow velocity of blood within the blood vessel over the heart cycle, or a volumetric flow value derived from the average flow velocity of blood within the vessel over the heart cycle and size of the vessel.

* * * * *